(12) United States Patent
Boyce-Jacino et al.

(10) Patent No.: US 6,872,521 B1
(45) Date of Patent: Mar. 29, 2005

(54) POLYMERASE SIGNALING ASSAY

(75) Inventors: Michael T. Boyce-Jacino, Finksburg, MD (US); Miriam B. Addelston, Baltimore, MD (US); Steven R. Head, Manchester, MD (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 09/097,791

(22) Filed: Jun. 16, 1998

(51) Int. Cl.[7] .............................. C12Q 1/68; C12Q 1/48; C12P 19/34

(52) U.S. Cl. ...................... 435/6; 435/91.1; 435/91.2; 435/15

(58) Field of Search ......................... 435/6, 91.1, 91.2, 435/15; 536/25.3

(56) References Cited

U.S. PATENT DOCUMENTS

| | | | |
|---|---|---|---|
| 4,521,509 A | 6/1985 | Benkovic et al. | 435/6 |
| 4,656,127 A | 4/1987 | Mundy | 435/6 |
| 4,812,856 A | 3/1989 | Wallace | 346/1.1 |
| 4,851,331 A | 7/1989 | Vary et al. | 435/6 |
| 4,981,783 A | 1/1991 | Augenlicht | 435/6 |
| 5,002,867 A | 3/1991 | Macevicz | 435/6 |
| 5,053,100 A | 10/1991 | Hayes et al. | 156/294 |
| 5,151,507 A | 9/1992 | Hobbs, Jr. et al. | 536/23 |
| 5,302,509 A | 4/1994 | Cheeseman | 435/6 |
| 5,445,934 A | 8/1995 | Fodor et al. | 435/6 |
| 5,503,980 A | 4/1996 | Cantor | 435/6 |
| 5,518,900 A | 5/1996 | Nikiforov et al. | 435/91.1 |
| 5,547,839 A | 8/1996 | Dower et al. | 435/6 |
| 5,599,695 A | 2/1997 | Pease et al. | 435/91.1 |
| 5,691,141 A | 11/1997 | Koster | 435/6 |
| 5,700,637 A | 12/1997 | Southern | 435/6 |
| 5,744,305 A | 4/1998 | Fodor et al. | 435/6 |
| 5,759,779 A | 6/1998 | Dehlinger | 435/6 |
| 5,795,714 A | * 8/1998 | Cantor et al. | 435/6 |
| 6,322,968 B1 | 11/2001 | Head et al. | 435/6 |
| 6,337,188 B1 | 1/2002 | Head et al. | 435/6 |

FOREIGN PATENT DOCUMENTS

| | | |
|---|---|---|
| WO | WO 89/10414 | 11/1989 |
| WO | WO 91/02087 | 2/1991 |
| WO | WO 92/15712 | 9/1992 |
| WO | WO 95/00669 | 1/1995 |
| WO | WO 95/03401 | 2/1995 |
| WO | WO 95/11995 | 5/1995 |
| WO | WO 96/13609 | 5/1996 |
| WO | WO 96/17957 | 6/1996 |
| WO | WO 97/26368 | 7/1997 |
| WO | WO 97/27317 | 7/1997 |
| WO | WO 98/49341 | 11/1998 |
| WO | 9927137 | 6/1999 |

OTHER PUBLICATIONS

Roger et al., Immobilization of Oligonucleotides onto a Glass Support via Disulfide Bonds: A Method for Preparation of DNA Microarrays, Analytical Biochemistry 266, 23–30 (1999).

(Continued)

*Primary Examiner*—Ardin H. Marschel
(74) *Attorney, Agent, or Firm*—Kalow & Springut LLP

(57) ABSTRACT

The present invention relates to the field of nucleic acid sequence analysis. The invention provides methods for performing a polymerase signal assay (PSA) to analyze nucleotide sequences using solid phase sequence arrays comprising a plurality of sequence reagents with primer sequences 4–6 bases in length. The methods of the invention generate a binary signal pattern which can be used to identify nucleic acid sequences and/or mutations and polymorphisms of a nucleic acid sequence. Mutations and polymorphisms which can be identified by the methods of the invention include single nucleotide polymorphisms (SNP's), base deletions, base insertions, and heterozygous as well homozygous polymorphisms.

25 Claims, 8 Drawing Sheets

OTHER PUBLICATIONS

Figure 1:
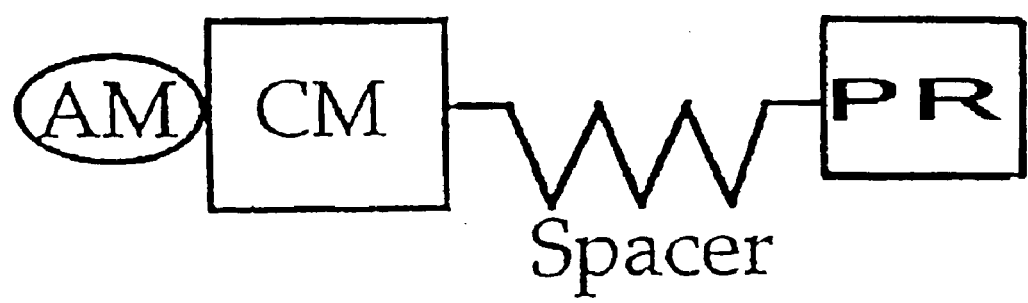

Head et al., Solid–phase Sequence Scanning for Drug Resistance Detection in Tuberculosis, Molecular and Cellular Probes 13, 81–87 (1999).

Guo et al., "Direct fluorescence analysis of genetic polymorphisms by hybridization with oligonucleotide arrays on glass supports,"*Nucleic Acids Research*, 22: 5456–5465 (1994).

Antrazhev et al., 1987, "3' substituted nucleoside phosphorothioates terminate DNA synthesis catalyzed by various DNA polymerases", Bioorg. Khim, 13:1045–1052.

Beattie et al., 1995, "Hybridization of DNA targets to glass–tethered oligonucleotide probes", Mol. Biotech., 4:213–225.

Beattie et al., 1991, "Solid phase gene assembly", Nature 352: 548–549.

Botstein et al., 1980, "Construction of a genetic linkage map in man using restriction fragment length polymorphisms", Am. J. Hum. Gen. 32:314–331.

Carlsson et al., 1991, "Short communication: solid phase disulfide oxides: a new approach to reversible immobilization and covalent chromatography of thiol compounds", Biotech. Applied Biochem. 14:114–120.

Chetverin et al., 1994, "Oligonucleotide arrays: new concepts and possibilities", Biotech 12:1093–1099.

Chidgeavadze et al., 1985, "3'–Fluoro–2',3'–dideoxyribonucleoside 5'triphosphates: terminators of DNA synthesis", FEBS Letters 183:275–278.

Chidgeavadze et al., 1986, "Nucleoside 5'–triphosphates with modified sugars as substrates for DNA polymerases", Biochem. Biophys. Acta 868:145–152.

Chidgeavadze et al., 1989, "Conformationally restricted 5'–triphosphates as termination substrates for DNA polymerases", Mol Bio. (Mosk.) 23:1732–1742.

Chu et al., 1988, "Ligation of oligonucleotides to nucleic acids or proteins via disulfide bonds", Nuc. Acids Res. 16:3671–3691.

Conner et al., 1983, "Detection of sickle cell $\beta^s$–globin allele by hybridization with synthetic oligonucleotides", PNAS 80:278–282.

Ekstein et al., 1976, "Synthesis and properties of diastereoisomers of adenosine 5'–(O–1–thiotriphosphate) and adenosine 5'–(O–thiotriphosphate)", Biochem. 15:1685–1691.

Engelke et al., 1988, "Direct sequencing of enzymaically amplified human genomic DNA", PNAS 85:544–548.

Fahy et al., 1993, "Design and synthesis of polyacrylamide–based oligonucleotide supports for use in nucleic acid diagnostics", Nuc. Acids Res. 21:1819–1826.

Gyllentsten et al., 1988, "Generation of single–stranded DNA by the Polymerase chain reaction and its application to direct sequencing of HLA–DQA locus", PNAS 85:7652–7656.

Haff et al., 1997, "Single–nucleotide polymorphism identification assays using a thermostable DNA polymerase and delayed extraction MALDI–TOF mass spectrometry", Genome Methods 7:378–388.

Herrlein et al., 1994, "57.3'–Amino–modified nucleotides useful as potent chain terminators for current DNA sequencing", Helvetica Chimica Acta 77:586–596.

Higuchi et al., 1985, "Production of single–stranded DNA templates by exonuclease digestion following the polymerase chain reaction", Nuc. Acids Res. 17:5865.

Holstrom et al., 1993, "A highly sensitive and fast nonradioactive method for detection of polymerase chain reaction products", Anal. Biochem. 209:278–283.

Jalanko et al., 1992, "Screening for defined cystic fibrosis mutations by solid–phase minisequencing", Clin. Chem. 38:39–43.

Kawai et al., 1993, "A simple method of detection amplified DNA with immobilized probes on microtitre wells", Alan. Biochem. 209:63–69.

Kornberg et al., 1992, In DNA replication, 2nd ed. eds: Freeman WH. & Co, San Francisco, pp408, 446–449.

Kornher et al., 1989, "Mutation detection using nucleotide analogs that alter electrophoretic mobility", Nucl. Acids Res. 17:7779–7784.

Kuppaswamy et al., 1991, "Single nucleotide primer extension to detect genetic diseases: experimental application to hemophilia B (factor IX) and cystic fibrosis gene", PNAS 88:1143–1147.

Lamture et al., 1994, "Direct detection of nucleic acid hybridization on the surface of a charge coupled device", Nuc. Acids Res. 22;2121–2125.

Landegren et al., 1988, "A ligase–mediated gene detection technique", Science 241:1077–1080.

Maskos et al., 1992, "Oligonucleotide hybridizations on glass supports: a novel linker for oligonucleotide synthesis and hybridization properties of oligonucleotides synthesized in situ", Nuc. Acids Res. 20:1679–1684.

Matteuci et al., 1981, "Synthesis of deoxyoligonucleotides on a polymer support", J. Am. Chem. Soc. 103:3185–3191.

Maxam et al., 1977, "A new method for sequencing DNA", PNAS 74:560.

Messing et al., 1983, "New M13 Vectors for cloning", Meth. Enzymol. 101:20.

Mihovilovic et al., 1989, "An efficient method for sequencing PCR amplified DNA", Biotechniques 7:14.

Mitsuya et al., 1986, "Inhibition of the in vitro infectivity and cytopathic effect of human T–lymphotrophic virus type III/lymphadenopathy–associated virus (HTLV–III/LAV) by 2',3'–didoxynucleosides", PNAS 83:1191.

Newton et al., 1993,"The production of PCR products with 5' single–stranded tails using primers that incorporated novel phosphramidite immediates", Nuc. Acids Res. 21:1155–1162.

Nickerson et al., 1990, "Automated DNA diagnostics using an ELISA–based oligonucleotide ligation", PNAS 87:8923–8927.

Nyren et al., 1993, "Solid phase DNA misequencing by enzymatic luminometric inorganic pyrophosphate detection assay", Anal. Biochem. 208:171–175.

Ott et al., 1987, "Protection of oligonucleotide primers against degradation by DNA polymerase I", Biochem. 8237–8241.

Pastinen et al., 1997, "Minisequencing: a specific tool for DNA analysis and diagnostics on oligonucleotide arrays", Genome Res. 7:606–614.

Pastinen et al., 1996, "Multiplex, fluorescent, solid–phase minisequencing for efficient screening of DNA sequence variation", Clin. Chem. 42:1391–1397.

Pease et al., 1994, "Light–generated oligonucleotide arrays for rapid DNA sequence analysis", PNAS 91:5022–5026.

Prober et al., 1987, "A system for rapid DNA sequencing with Fluorescent chain–terminating dideoxynucleotides", Science 238: 336–340.

Prezant et al., 1992, "Trapped–oligonucleotide nucleotide incorporation (TONI) assay, a simple method for screening point mutations", Hum. Mut. 1:159–164.

Rasmussen et al., 1991, "Covalent immobilization of DNA onto polystyrene microwells: the molecules are only bound at the 5' end", Anal. Biochem. 138–142.

Running et al., 1990, "A procedure for productive coupling of synthetic oligonucleotides to polystyrene microtitre wells for hybridiztion capture", Biotechniques 8:276–277.

Sanger et al., 1975, "A rapid method for determining sequences in DNA by primed synthesis with DNA polymerase", J. Mol. Bio. 94:441.

Sayers et al. 1988, 5'–3–exonucleases in phosphorothioate–based oligonucleotide–directed mutagenesis, Nuc Acid Res. 16:791–802.

Shumaker et al., 1996, "Mutation detection by solid phase primer extension", Hum. Mutat. 7:346–354.

Sliwkowski et al., 1983, "Resolution of sulphydryl oxidase from γ–glutamyltransferase in bovine milk by covalent chromatography on cysteinylsuccinoamidopropyl–glass", Biochem. J. 209:731–739.

Smith et al., 1994, "Direct fluorescence analysis of genetic polymorphisms by hybridization with oligonucleotide arrays on glass supports", Nuc. Acids Res. 22:5456–5465.

Sokolov B., "Primer extension technique for the detection of single nucleotide in genomic DNA", Nuc. Acids Res. 18:3671, 1990.

Southern et al., 1994, "Arrays of complementary oligonucleotides for analyzing the hybridization behavior of nucleic acids", Nuc. Acids Res. 22:1368–1373.

Spiegelman S., 1964, "Hybrid nucleic acids", Sci. Am. 210:48.

Syvanen et al., 1990, "A primer–guided nucleotide incorporation assay in genotyping of alipoprotein E", Genomics 8:684–692.

Ugozzoli et al., 1992, "Detection of specific by using specific primer extension followed by capture on solid support", GATA 9:107–112.

White et al., 1988, "Chromosome mapping with DNA markers", Sci. Am. 258:40–48.

Wong et al., 1987, "Characterisation of β–thalassaemia mutations using direct genomic sequencing of an amplified single copy DNA", Nature 330:384–386.

Yuzhakov et al, 1992, "3'–Mercapto–2'3'–dideoxynucleotides are high effective terminators of DNA synthesis catalysed by HIV reverse transcriptase", FEBS Letters 306:185–188.

* cited by examiner

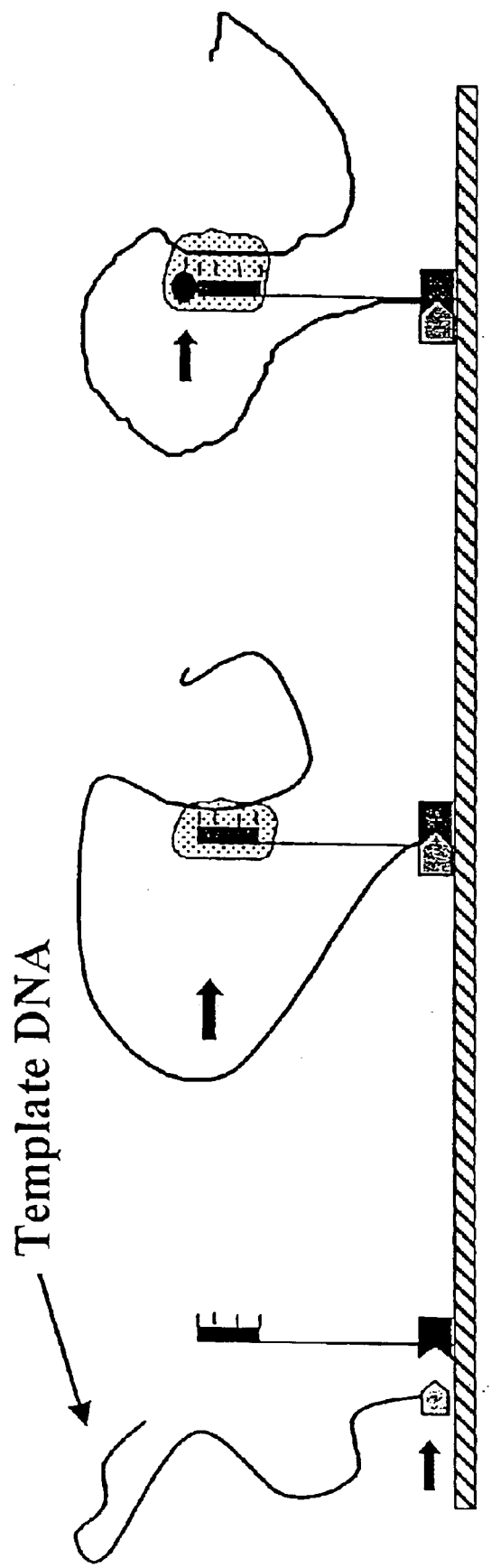

FIG. 3A
EXPECTED DATA SIGNALS
WILD TYPE
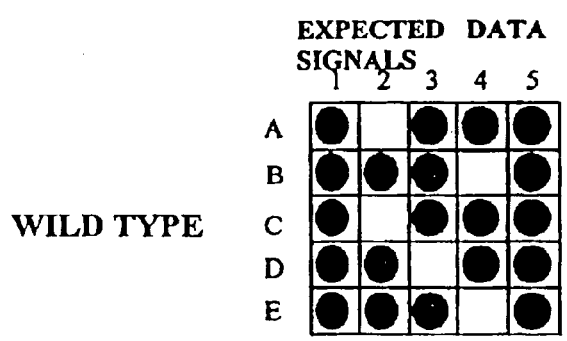
FIG. 3B
EXPERIMENTAL DATA
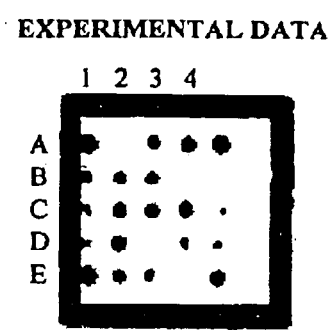
MUTANT
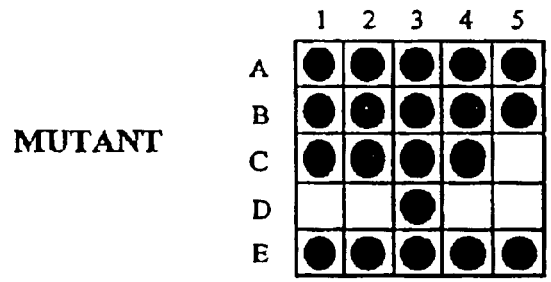
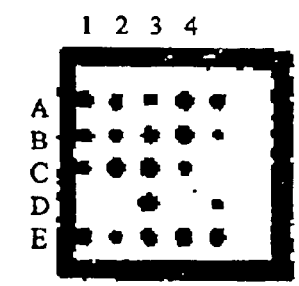
FIG. 3C
FIG. 3D

POLYMERASE SIGNALING ASSAY

1. FIELD OF THE INVENTION

The present invention relates to the field of nucleic acid sequence analysis. Specifically, the invention provides methods of nucleic acid sequence analysis which use combinatorial sequence array primers to sequence and/or detect mutations or polymorphisms within a template nucleic acid.

2. BACKGROUND OF THE INVENTION

This invention relates to the field of nucleic acid sequence analysis. The analysis of nucleic acid sequences can be used, e.g., to determine the presence or absence of a particular genetic element. Variant genetic elements of a nucleic acid sequence usually exist. Exemplary variant genetic elements may include, but are by no means limited to, genetic mutations or polymorphisms such as single nucleotide polymorphisms ("SNP's"), base deletions, base insertions, and heterozygous as well as homozygous polymorphisms. Accordingly many techniques have been developed to compare homologous segments of nucleic acid sequence to determine if the segments are identical or if they differ at one or more nucleotides. Practical applications of these techniques include genetic disease diagnoses, infectious disease diagnoses, forensic techniques, paternity determinations, and genome mapping.

In general, the detection of nucleic acids in a sample and of the subtypes thereof depends on the technique of specific nucleic acid hybridization in which the oligonucleotide probe is annealed under conditions of high stringency to nucleic acids in the sample, and the successfully annealed probes are subsequently detected (see, e.g., Spiegelman, S., 1964, *Scientific American* 210:48).

The most definitive method for comparing DNA segments is to determine the complete nucleotide sequence of each segment. Examples of how sequencing has been used to study mutations in human genes are included in the publications of Engelke et al. (1988, *Proc. Natl. Acad. Sci. U.S.A.* 85:544–548) and Wong et al. (1987, *Nature* 330:384–386). The most commonly used methods of nucleic acid sequencing include the dideoxy-mediated chain termination method, also known as the "Sanger Method" (Sanger, F. et al., 1975, *J. Molec. Biol.* 94:441; Porbe, J. et al., 1987, *Science* 238:336–340) and the chemical degradation or "Maxam-Gilbert" method (Maxam, A. M. et al., 1977, *Proc. Natl. Acad. Sci. U.S.A.* 74:560).

Both the Sanger and Maxim-Gilbert methods comprise a series of four chemical reactions, one for each of the nucleotide bases, e.g., A, C, G, and T for DNA, consisting of either primer extension (Sanger) or partial cleavage (Maxim-Gilbert) reactions. The reactions produce four sets of nested nucleic acid molecules whose lengths are determined by the location of a particular base along the length of the nucleic acid molecule being sequenced. The nested reaction products are then resolved by electrophoretic gels.

The separation and analysis of reaction products on electrophoretic gels is a laborious and time consuming step. Accordingly, alternative methods have been developed to sequence nucleic acid molecules. For example, there is considerable interest in developing methods of de novo sequencing using solid phase arrays (see, e.g., Chetverin, A. B. et al., 1994, *Bio/Technology* 12:1093–1099; Macevicz, U.S. Pat. No. 5,002,867; Beattie, W. G. et al., 1995, *Molec. Biotech.* 4:213–225; Drmanac, R. T., EP 797683; Gruber, L. S., EP 787183; each of which is incorporated herein by reference in its entirety). These methods consist primarily of hybridization of template nucleic acids to arrayed primers containing combinatorial sequences which hybridize to complementary sequences on the template strand. The methods combine the capture of the template, by formation of stable duplex structures, with sequence discrimination due to instability of mismatches between the template and the primer.

Such methods must typically employ arrays of primers at least twelve bases in length which contain approximately 16 million sequence combinations. Such arrays are very complex and time consuming both to construct and to analyze. Thus, at the present time it is not practical to use extensive sequencing methods, such as the methods described above, to compare more than just a few DNA segments because the effort required to determine, interpret, and compare complete sequence information is time-consuming.

Restriction fragment length polymorphism ("RFLP") mapping is another commonly used screen for DNA polymorphisms arising from DNA sequence variation. RFLP consists of digesting DNA with restriction endonucleases and analyzing the resulting fragment by means of Southern blots, as described by Botstein et al., 1980 (*Am. J. Hum. Genet.* 32:314–331) and White et al. (1988, *Sci. Am.* 258:40–48). Mutations that affect the recognition of sequence of the endonuclease will preclude enzymatic cleavage at that site, thereby altering the cleavage pattern of the DNA. DNAs are compared by looking for differences in restriction fragment lengths. However, a major problem with RFLP mapping is its inability to detect mutations that do not affect cleavage with a restriction endonuclease. Thus, many mutations are missed with this method. Further, the methods used to detect restriction fragment length polymorphisms are very labor intensive, particularly the techniques involved with Southern blot analysis.

Alternative, simpler methods have been developed which use solid phase arrays to analyze single nucleotide polymorphisms (SNP's). These techniques rely on the fact that analysis of SNP's, which constitute sites of variation flanked by regions of invariant sequence, requires no more than the determination of the identity of the single nucleotide present at the site of variation.

For example, several primer-guided nucleotide incorporation procedures for assaying polymorphic sites in DNA have been described (e.g., Komher, J. S. et al., 1989, *Nucl. Acids Res.* 177779–7784; Sokolov, B. P., 1990, *Nucl. Acids Res.* 18:3671; Syvanen, A.-C. et al., 1990, *Genomics* 8:684–692; Kuppuswamy, M. N. et al., 1991, *Proc. Natl. Acad. Sci. U.S.A.* 88:1143–1147; Prezant, T. R. et al., 1992, *Hum. Mutat.* 1:159–164; Ugozzoli, L. et al., 1992, GATA 9:107–112; Nyren, P. et al., 1993, *Anal. Biochem.* 208:171–175; and Wallace WO89/10414). Each of these methods relies on the incorporation of labeled deoxynucleotides to discriminate between bases at a polymorphic site. An alternative microsequencing method, the Genetic Bit Analysis (GBA™) method has been disclosed by Goelet, P. et al. (WO 92/15712) which avoids many of the problems in the above identified microsequencing assays. In GBA™, the nucleotide sequence information surrounding a predetermined site of interrogation is used to design an oligonucleotide primer that is complementary to the region immediately adjacent to, but not including, the predetermined site. The target DNA template is selected from the biological sample and hybridized to the interrogating primer. This primer is extended by a single labeled dideoxynucleotide using DNA polymerase in the presence of at least two, and most preferably all four chain terminating nucleoside triphosphate precursors.

Several variations of the GBA method have been developed, as well as other microsequencing methods (see, e.g., Mundy, U.S. Pat. No. 4,656,127; Vary and Diamond, U.S. Pat. No. 4,851,331; Cohen, D. et al., PCT Application No. WO91/02087; Chee, M. et al., WO95/11995; Landegren, U. et al., 1988, Science 241:1077–1080; Nicerson, D. A. et al., 1990, Proc. Natl. Acad. Sci. U.S.A. 87:8923–8927; Pastinen, T. et al. (1997, Genome Res. 7:606–614; Pastinen, T. et al., 1996, Clin. Chem. 42:1391–1397; Jalanko, A. et al. (1992, Clin. Chem. 38:39–43; Shumaker, J. M. et al., 1996, Hum. Mutation 7:346–354; Caskey, C. et al., WO 95/00669). Although they are simpler to perform and analyze than de novo sequencing, such microsequencing methods require primers that hybridize to the target nucleic acid molecule at a site immediately adjacent to a polymorphism (or a site suspected of being next to a polymorphism). Hence, such techniques require prior knowledge of a "wild type" nucleic acid sequence. Further, the techniques are limited to identifying a specific mutation or polymorphisms, typically a SNP, at a specific location in a specific nucleic acid sequence. Finally, such techniques also typically require multiple interrogations per target base.

3. SUMMARY OF THE INVENTION

The present invention relates to a unique universal array system and its use for nucleic acid sequence analysis. The array system of the invention can be used for nucleic acid sequence analysis, for example to identify DNA and other nucleic acid sequences as well as mutations and polymorphisms in those sequences.

The principles of the sequence analysis system and methods of the invention involve: (i) capture of the polynucleotide to be analyzed, referred to herein as the "template" by a specific "capture moiety" at a particular "capture region" on the template, (ii) scanning of the template by a combinatorial primer-polymerase complex for regions of complementarity, and (iii) signal generation through a template homology dependent primer extension reaction wherein the primer is extended by one or more nucleotides or nucleotide analogues.

Because primer extension occurs only when a region of complementarity to the primer is encountered on the template, the extension signal generated in step (iii) is the key element that identifies the existence of a specific nucleic acid sequence in the template polynucleotide. If no sequence complementary to the combinatorial primer is present in the template, primer extension does not occur, and an extension signal is not generated. Thus, by performing the methods of the invention with an array comprising a plurality of combinatorial primers, a unique pattern or matrix of extended vs. non-extended primer signals is generated for the polynucleotide sequence being analyzed.

In a preferred embodiment, the array system of the invention comprises an array of sequence reagents arrayed on a solid support, and comprising (a) a capture moiety which can form a stable complex with a region of a template, (b) a spacer region, and (c) a primer region comprising 3–7 bases which, in the presence of a polymerase, can recognize complementary sequences in the template and can be extended by one or more nucleotides moieties (i.e., nucleotides or nucleotide analogues) by a template dependent primer extension reaction. Most preferably, the invention is practiced using a universal sequencing array, as describe by Head, S. et al. (U.S. patent application Ser. No. 08/976,427, filed Nov. 21, 1997).

Preferably, the nucleotide moieties used for template dependent primer extension are labeled nucleotides. In various embodiments, the nucleotide moieties may be, e.g., chain terminating nucleotides such as dideoxynucleotides, or nucleotides that are not chain terminating such as deoxynucleotides. Preferably, the nucleotide moieties comprise nucleotides or nucleotide analogues for all four of the nucleotide bases, A, G, C, and T.

The invention is based, in part, on Applicants' discovery that nucleic acid sequences can be analyzed on solid-phase arrays, referred to herein as sequence arrays, through the novel analysis of "on/off" polymerase extension signals on the arrays. The methods do not require that the actual identity of the polymerase extension product be determined, merely the determination of whether a polymerase extension product is or is not present for each element of the array. Subsequences of the template nucleic acid molecule can then be identified through simple analysis of these on/off polymerase extension signals, and mutations and polymorphisms in the template nucleic acid molecule are thereby detected.

The present invention overcomes the limitations in the prior art by providing methods for the analysis of nucleic acid sequences which employ arrays of primer sequences that are three to seven bases in length. Such primer arrays have no more than 4096 possible sequence combinations (for six bases), and can successfully analyze polynucleotides of up to several thousand bases. In one preferred embodiment, such an array will have only 1024 sequence combinations (for five bases), and can analyze the sequence of a polynucleotide having up to about 1000 bases. In another preferred embodiment, such an array will have only 256 sequence combinations (for four bases), and can analyze sequences of up to about 300 bases. In certain other embodiments, it is possible to use arrays having even fewer sequence combinations. Such simple arrays are significantly easier to manufacture and screen than the solid phase arrays typically used for de novo sequencing techniques, which comprise millions of sequence combinations and/or employ sequences derived empirically from the target sequence.

The methods of the present invention also provide a method for analyzing nucleic acid sequences wherein a "binary" polymerase extension signal is generated for each primer in the array. Thus, signal analysis simply comprises detecting the presence or absence of a polymerase extension product. Neither identification of the extension product, nor discrimination between the different extension products is required.

Signal analysis is further simplified in the present invention in that analysis of the resulting signals simply comprises analyzing the binary signal pattern or "matrix" of the primer array. The pattern is then used to determine the presence or absence of a mutation, a polymorphism, or the sequence of a target nucleic acid molecule. Thus, the methods of the invention utilize a pattern matching approach to sequence analysis, thereby reducing or even eliminating the need for complicated or intensive methods of analysis.

The present invention further improves upon the prior art in that no prior knowledge of the nucleic acid sequence to be analyzed is required to practice the methods of the invention. The methods of the invention can also be used to detect any mutation or polymorphism at any location in a nucleic acid molecule, and are not limited to assaying for a particular mutation or SNP. Thus, the methods of the present invention are not limited to merely determining the identity of a nucleotide base at a specific position in a nucleic acid molecule. Examples of mutations and polymorphisms which can be detected by the present invention include, but are by no means limited to, single nucleotide polymorphisms (SNP's), as well as base deletions, base insertions, and heterozygous mutations and polymorphisms.

The solid phase arrays used by the methods of the invention are simple to produce, and analysis of the resulting on/off polymerase extension signals is simple and straightforward, reducing the need for complicated, intensive methods of analysis. Indeed, the PSA methods of the invention are ideally suited for simple pattern matching methods of analysis.

4. BRIEF DESCRIPTION OF THE DRAWINGS

FIG. 1 is a diagrammatic representation of the structure of the sequence reagent used in the methods of the present invention.

FIGS. 2A–C illustrate the steps of the polymerase signaling assay (PSA) of the present invention; FIG. 2A illustrates the "capture" step wherein the capture region of the template nucleic acid molecule forms a stable complex with the capture moiety of a sequence reagent; FIG. 2B illustrates the "scan" step wherein the primer region of the sequence reagent recognizes a complementary region of the template nucleic acid molecule; FIG. 2C illustrates the "signal" step wherein the primer is extended by one or more nucleotides.

FIGS. 3A–D illustrates the expected (FIG. 2A, FIG. 2C) and experimental (FIG. 3B, FIG. 3D) data signals from PSA analysis of the "wild type" and "mutant" nucleic acid sequences shown in Table 1, using a sequence array comprising the 21 primer sequences listed in Table 2.

Figure 4C:
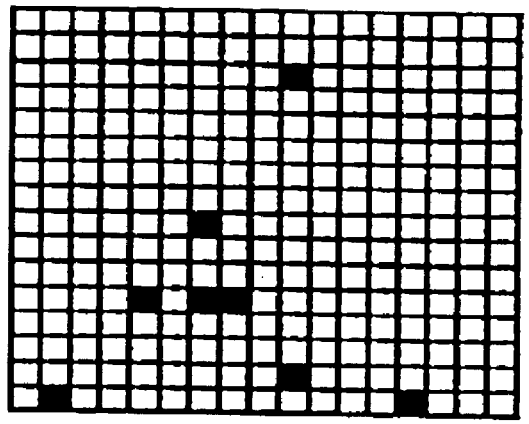
Figure 4B:
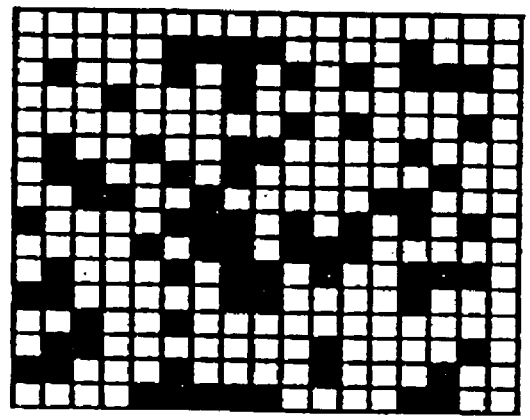
Figure 4A:
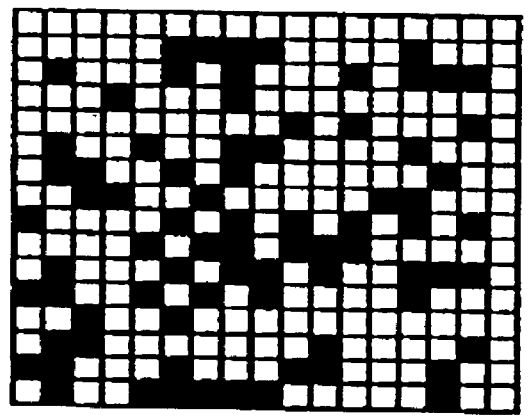

FIGS. 4A–C illustrates data signal patterns predicted for PSA analysis of p53 exon 8; FIG. 4A illustrates the PSA data signal pattern for a wild type p53 template; FIG. 4B illustrates the PSA data signal pattern of a p53 template having a single nucleotide polymorphism (SNP; 38C→T); FIG. 4C illustrates the difference between the two data signal patterns shown in FIGS. 4A–B.

Figure 5C:
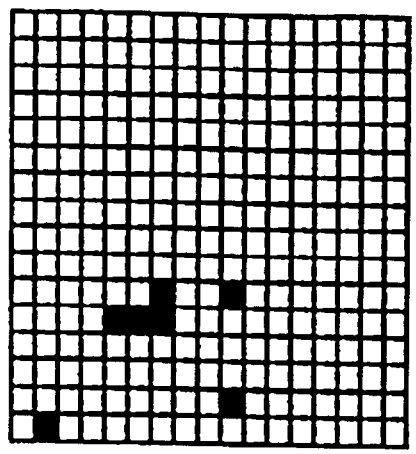
Figure 5B:
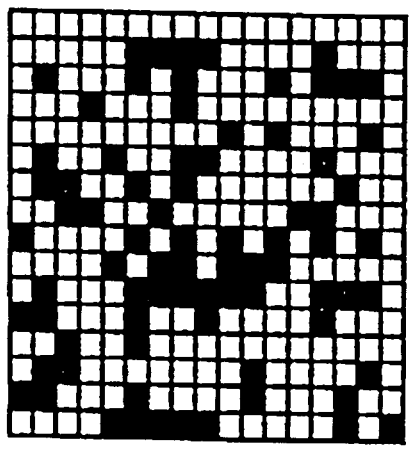
Figure 5A:
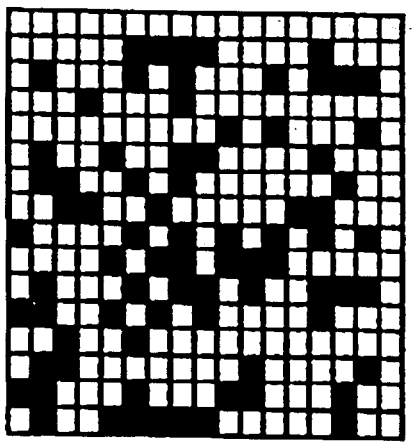

FIGS. 5A–C illustrates predicted data signal patterns for PSA analysis of p53 exon 8; FIG. 5A illustrates the data signal pattern of a wild type p53 template; FIG. 5B illustrates the data signal pattern of a p53 template having the SNP 38C→A; FIG. 5C illustrates the difference between the two data signal patterns shown in FIGS. 5A–B.

Figure 6C:
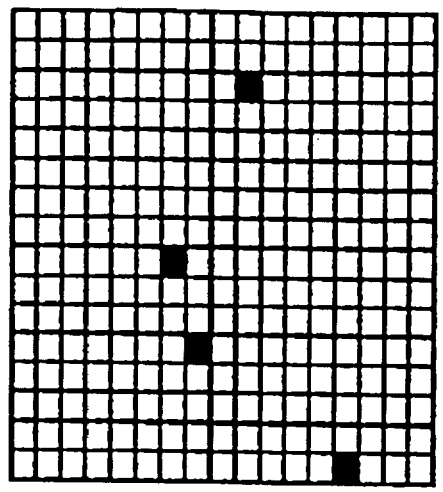
Figure 6B:
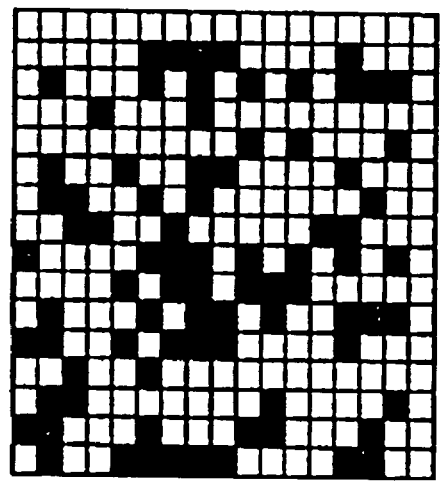
Figure 6A:
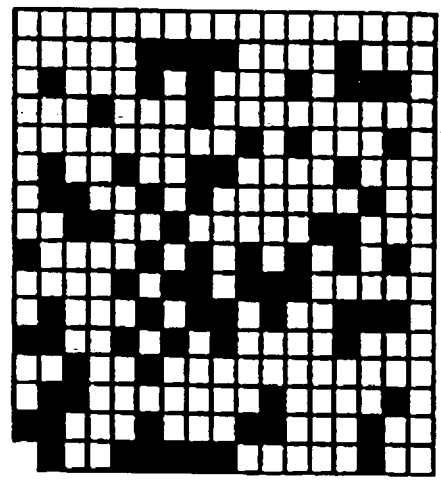

FIGS. 6A–C illustrates predicted data signal patterns for PSA analysis of p53 exon 8; FIG. 6A illustrates the data signal pattern obtained for a wild type p53 template; FIG. 6B illustrates the data signal pattern of a p53 template having a the heterozygous polymorphism 38C→A; FIG. 6C illustrates the difference between the two data signal patterns shown in FIGS. 6A–B.

Figure 7C:
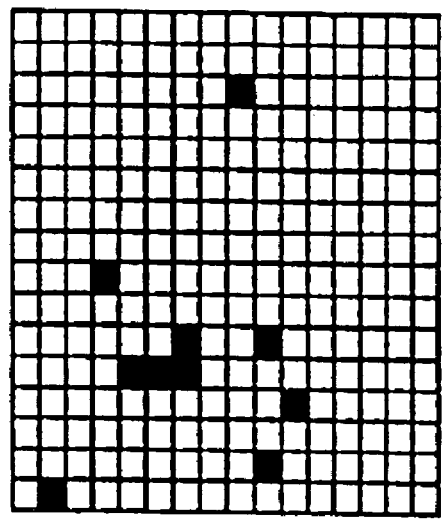
Figure 7B:
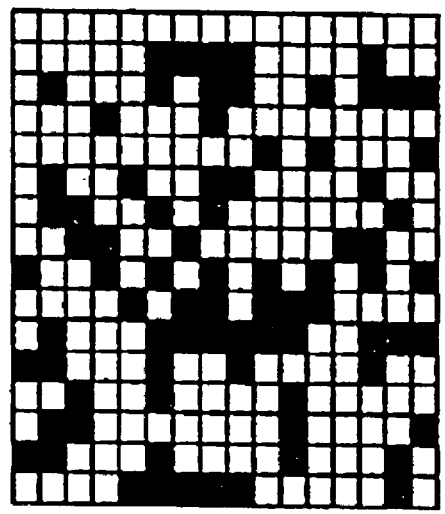
Figure 7A:
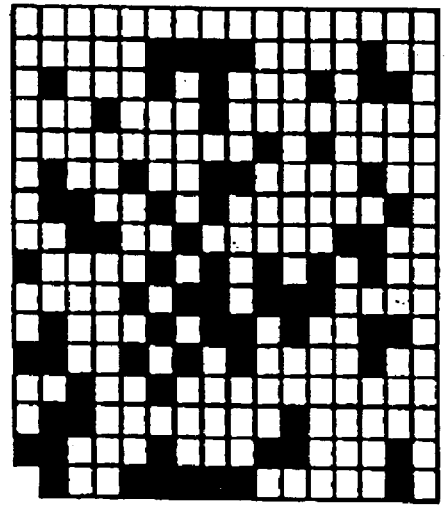

FIGS. 7A–C illustrates predicted data signal patterns for PSA analysis of p53 exon 8; FIG. 7A illustrates the data signal pattern of a wild type p53 template; FIG. 7B illustrates the data signal pattern for PSA analysis of a p53 template having a five base deletion; FIG. 7C illustrates the difference between the two data signal patterns shown in FIGS. 7A–B.

Figure 8C:
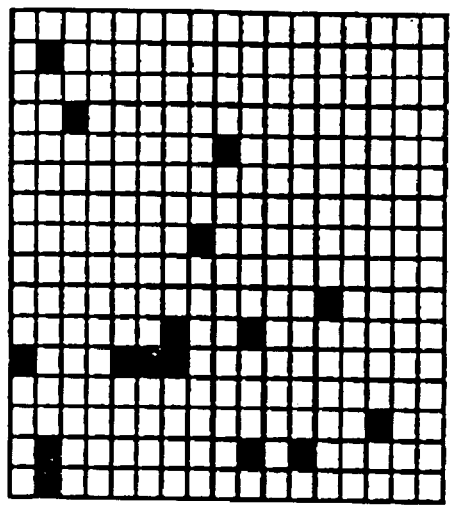
Figure 8B:
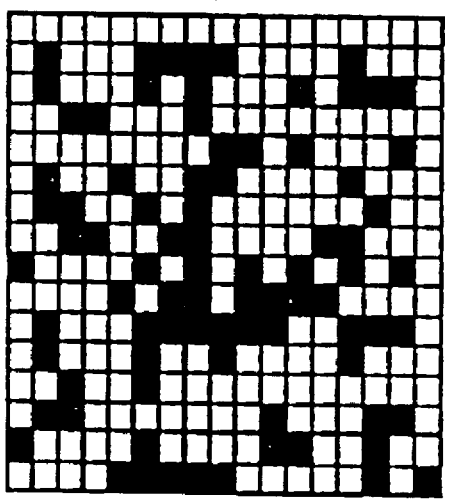
Figure 8A:
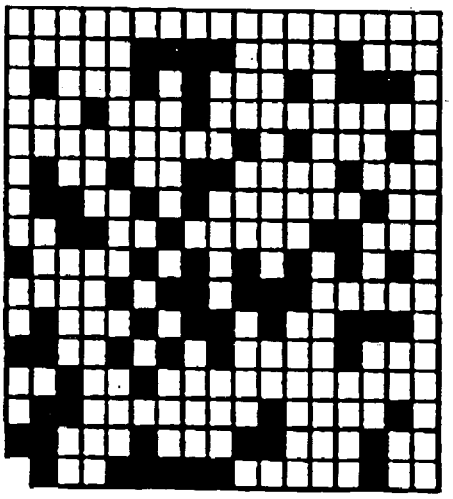

FIGS. 8A–C illustrates predicted data signal patterns for PSA analysis of p53 exon 8; FIG. 8A illustrates the data signal pattern obtained for a wild type p53 template; FIG. 8B illustrates the data signal pattern for PSA analysis of a p53 template having a five base insertion; FIG. 8C illustrates the difference between the two data signal patterns shown in FIGS. 6A–B.

5. DETAILED DESCRIPTION OF THE INVENTION

The present invention includes methods of an assay referred to herein as the polymerase signaling assay or PSA. These methods are used for analyzing the sequence of nucleic acid molecules. A nucleic acid molecule which is sequence analyzed by the methods of this invention is defined herein as a template nucleic acid molecule, or template molecule, or template. Template nucleic acid molecules which may be sequence analyzed by the methods of the invention include DNA molecules, such as, but by no means limited to, genomic DNA molecules, cDNA molecules, and fragments thereof. Template nucleic acid molecules which may be sequence analyzed by the methods of the invention also include RNA molecules, such as, but by no means limited to, messenger RNA (mRNA) molecules, ribosomal RNA (rRNA) molecules, and fragments thereof.

The nucleic acid molecule to be analyzed by the PSA methods of this invention may be from any source. For example, the template nucleic acid molecule may be a naturally occurring nucleic acid molecule such as a genomic or extragenomic DNA molecule isolated from an organism, or an RNA molecule, such as an mRNA molecule, isolated from an organism. Alternatively, the template nucleic acid molecule may be synthesized, including, e.g., nucleic acid molecules synthesized enzymatically in vivo or in vitro, such as, for example, a cDNA molecule, or a nucleic acid molecule synthesized by PCR. The sample of nucleic acid molecules can comprise, e.g., molecules of deoxyribonucleic acid, ribonucleic acid, or copolymers or deoxyribonucleic acid and ribonucleic acid.

The invention is based, in part, on the discovery by applicants that nucleic acid sequences can be analyzed on solid phase arrays, referred to herein as sequence arrays, through the novel analysis of "on/off" polymerase extension signals on the arrays. The methods do not require that the actual identity of the polymerase extension product be determined, merely the determination of whether a polymerase extension product is or is not present for each element of the array. Subsequences of the template nucleic acid molecule can then be identified through simple analysis of these on/off polymerase extension signals, and mutations and polymorphisms in the template nucleic acid molecule are thereby detected.

The solid phase arrays used by the methods of the invention are simple to produce, and analysis of the resulting on/off polymerase extension signals is simple and straightforward, reducing the need for complicated, intensive methods of analysis. Indeed, the PSA methods of the invention are ideally suited for simple pattern matching methods of analysis.

The following subsections present the methods of the invention in greater detail. In particular, Section 5.2 first describes the sequence arrays used in the methods of the present invention, as well as methods for preparing such arrays. The methods of the polymerase signaling assay are then described, in detail, in Section 5.3.

5.1. Sequence Arrays

Sequence arrays such as those used in the methods of the present invention are described, in detail, by Head, S. et al. (U.S. application Ser. No. 08/976,427, filed Nov. 21, 1997), which is incorporated herein by reference in its entirety. Such sequence arrays are also discussed below, as they pertain specifically to the PSA methods of the present invention.

The sequence arrays of the present invention comprise solid phase arrays of combinatorial oligonucleotides. Such arrays comprise a plurality of sequencing reagents immobilized, either individually or in a group, to a solid surface in a spatially distinct fashion. The sequence reagents of the sequence arrays each comprise (i) a "capture moiety", (ii) a "spacer region", and (iii) a combinatorial primer, or "primer region" which is also referred herein as the primer sequence. The methods of the present invention utilize sequence arrays wherein the primer of each sequencing reagent preferably comprises from four to six bases which can recognize a complementary sequence of a template nucleic acid molecule.

5.1.1. The Sequence Reagent

The sequence reagents of the sequence arrays used in the PSA methods of the present invention are designed for use as part of a combinatorial array for primer extension-based sequence analysis of template nucleic acid molecules. A specific, preferred embodiment of the sequence reagent is illustrated in FIG. 1. The individual components of the sequence reagent, which are illustrated in FIG. 1, are described below.

Attachment Moiety:

Under one preferred embodiment, the sequence reagent includes an optional "attachment moiety" (FIG. 1; AM) which is coupled to one terminus of the sequencing reagent, preferably the 5'-terminus, and functions to attach the sequence reagent to the solid surface. Preferably the attachment moiety specifically attaches the sequence reagent to the solid surface.

In an alternative embodiment, the sequence reagent is non-specifically attached to the solid surface. The sequence reagent can be non-specifically attached to the solid surface, e.g., by means of a cationic agent, such as octyldimethylamine Hcl or NaCl. Alternatively, the sequence reagent can be non-specifically attached to a charged surface, such as an amino modified solid surface.

Under another preferred embodiment, the sequencing reagent is specifically attached to the solid surface. Preferably, the specific attachment of the sequence reagent is by means of a reversible bond.

Under one preferred embodiment, the sequencing reagent can be specifically attached to the solid surface by means of a non-covalent bond. For example, a biotin or iminobiotin labeled oligonucleotide may be immobilized to an avidin or strepavidin coated solid surface. Alternatively, a haptenated oligonucleotide may be immobilized to an antibody coated solid surface. However, it is to be understood that other ligand receptor interactions are suitable for use in the present invention.

Under another preferred embodiment, the sequencing reagent is specifically attached to the solid surface by means of a covalent bond. Preferably, the covalent bond is a disulfide bond. Additional embodiments for attaching the sequencing reagent to the solid surface are discussed below with respect to the capture moiety. The various embodiments for immobilizing a nucleotide to a solid surface discussed with respect to the capture moiety, described below, can also be applied to immobilize the present sequencing nucleotides to a solid surface.

Exemplary attachment moieties suitable for use in the present invention therefore include the incorporation of an amino, thiol, disulfide, biotin, etc. group at the 5'-terminus of the sequence reagent. This modification can be done either at the time the sequence reagent is synthesized, or after synthesis of the sequence reagent.

Capture Moiety:

The "capture moiety" (FIG. 1; CM) of the sequence reagent is a moiety which is capable of forming a stable complex with a region of the template nucleic acid molecule, referred to herein as the "capture region" of the template molecule. The capture moiety can be near either the 5' or 3' terminus of the sequence reagent.

The capture moiety can be, e.g., a DNA, RNA, or PNA (protein nucleic acid) sequence. The nucleic acid sequence may also contain modified bases. For example, a RNA sequence may contain 2'-O-methoxy RNA, and a DNA sequence may contain 5-Me-dC, pdC, pdU, or 2-amino-dA. Under another embodiment, the nucleic acid sequence may contain a modified backbone wherein the backbone is modified with phosphorothioate, phosphordithioate, methylphosphonate, or H-phosphonate.

Under another preferred embodiment, the capture moiety may be biotin, iminobiotin, avidin, strepavidin, antibody, hapten, a receptor, a ligand, or a charged base. Receptors and ligands suitable for use in the capture moiety include, but are not limited to, protein A, protein G, the Fc portion of an antibody, or Fc receptor.

The capture moiety can also form a stable complex with the capture region of the template nucleic acid molecule, e.g., by means of a disulfide bond, a covalent ether or thioether linkage via an epoxy, UV cross-linkage, a condensation reaction with a carbodiimide, a bromoacetyl/thiol linkage to a thioester, a crosslinkage with a bi-functional group, or a complex between thiol and gold. Bi-functional crosslinking reagents suitable as capture moieties in the present invention include, but are not limited to, an imidiester, N-hydroxysuccinimidyl ester, malemide, alkyl halide, aryl halide, alpha-haloacyl, and pyridyl disulfide. The capture moiety can also be covalently attached, e.g., by means of a labeling group. Labeling groups suitable for use in the present invention include, but are not limited to, amino, sulfhydryl, disulfide, phosphate, thiophosphate, dithiophosphate, and psoralen groups.

The capture moiety can also exist as a separate molecule that is co-attached to the solid phase and effectively brings the template into close proximity to the primer region of the sequence reagent (FIG. 1; PR).

In one of the preferred embodiments, the capture moiety comprises a sequence of 8–24 cytosine bases which can hybridize to a sequence of 8–24 guanine bases incorporated on the template strand. In another preferred embodiment, the capture moiety comprises a specific sequence complementary to a PCR primer, or portion thereof, used to amplify a region of the template strand. For example, the capture moiety can comprise a sequence complementary to a restriction site found within the PCR primer. Alternatively, the PCR primer hybridizes to a promoter site and thus, the capture sequence is the same sequence as a promoter site. PCR primer design is well known to those of skill in the art and it is appreciated that the capture sequence can be complementary to a PCR primer, to a portion thereof, or to a modification thereof.

The efficiency of hybridization and the thermal stability of hybrids formed between the target nucleic acid and a short oligonucleotide probe depends strongly on the nucleotide sequence of the probe and the stringency of the reaction conditions (see, e.g., Conner, B. J. et al., 1983, *Proc. Natl. Acad. Sci. U.S.A.* 80:278–282). Appropriate hybridization conditions for specific embodiments of the capture moiety and capture region will therefore be apparent to those skilled in the art, in view of the above and other references well known in the art.

Spacer Region:

The sequence reagent additionally comprises a spacer region (FIG. 1; Spacer). Preferably, the spacer region is at least 10 nm in length, more preferably 10–100 nm in length. However, the spacer region can also be greater than 100 nm in length. Spacer regions suitable for use in the present invention include, but are not limited to, DNA or RNA sequence, PNA sequence, polyethylene glycol groups, 5-nitro-indole groups, or other chemical spacer arms. The spacer region can also consist of analogues of DNA, RNA, and PNA. In such embodiments, the nucleic acid sequences of the spacer region may comprise unmodified or modified nucleotide bases, such as the modified bases described above for the capture moiety. Preferably, the spacer region consists of a random sequence of bases. However, the spacer region can also consist of a pseudo-random or non-random sequence of bases.

The spacer region is preferably designed to minimize template independent noise. Template independent noise is the result of signal detection independent (i.e., in the absence) of the template molecule. Under one embodiment, a spacer region is additionally placed in between the capture moiety and the attachment moiety.

Primer Region:

Finally, the sequence reagent also comprises a primer region (FIG. 1; PR), also referred to herein as the primer. The primer region consists of specific bases which can recognize sequences on the template strand, and can be extended by a polymerase with one or more labeled nucleotides. In particular, as used in the PSA methods of the present invention, the primer consists of four to six specific bases which can recognize complementary sequences on the template strand. Generally, the primer will comprise a DNA or RNA sequence four to six of the naturally occurring nucleotide bases. Such sequences are also referred to herein as the primer sequences of the sequence reagent.

The primer sequence may be, e.g., an oligodeoxyribonucleotide, and oligoribonucleotide, or a copolymer of deoxyribonucleotides and ribonucleotides. The primer sequence can be synthesized either enzymatically in vivo, enzymatically in vitro, or non-enzymatically in vitro, e.g., by the methods described in Section 5.1.2 below.

The primer sequence, or alternatively the sequence reagent, may also be labeled with a detectable marker or label, including the detectable labels described in Section 5.2.4, below. Preferably the detectable label of marker used to label the primer or sequence reagent will be different from the labels used to label either the extended primer, or the template.

5.1.2. Synthesis of a Sequencing Reagent

There are two preferred methods for making the sequencing reagents of a sequence array. The first method is to synthesize the specific oligonucleotide sequences directly on the solid-phase (in situ) in the desired pattern (i.e., in the desired spatially distinct fashion), as described, e.g., by Southern et al. (1994, Nucl. Acids Res. 22:1368–1373), by Maskos et al. (1992, Nucl. Acids Res. 20:1679–1684), and by Pease et al. (1994, Proc. Natl. Acad. Sci. U.S.A. 91:5022–5026). The other method is to first pre-synthesize the oligonucleotides in an automated DNA synthesizer, such as an ABI 392, and to then attach the synthesized oligonucleotides onto the solid-phase at specific locations (see, e.g., Lamture et al., 1994, Nucl. Acids Res. 22:2121–2125; and Smith et al., 1994, Nucl. Acids Res. 22:5456–5465).

In the first method, the efficiency of the coupling step of each base will affect the quality and integrity of the nucleic acid molecule array. This method generally yields a large percentage of undesired incomplete (i.e., shortened) sequence which can create problems in the analysis step, and thereby effect the integrity of the analysis. Thus, the quality and integrity of an array synthesized according to the first method is inversely proportional to the length of the nucleic acid molecule. Specifically, the synthesis of longer oligonucleotides results in a higher percentage of incomplete, shortened sequences.

The second, more preferred method for nucleic acid array synthesis utilizes an automated DNA synthesizer for DNA synthesis. Oligonucleotides are synthesized using standard phosphoramidite chemistry (see, e.g., Matteucci, M. D. et al., 1981, J. Amer. Chem. Soc. 103:3185–3191). Preferably, a segmented synthesis strategy is used to simultaneously synthesize large numbers of oligonucleotides (see, e.g., Beattie, K. L. et al., 1988, Appl. Biochem. Biotechnol. 10:510–521; Beattie, K. L. et al., 1991, Nature 352:548–549). The controlled chemistry of an automated DNA synthesizer allows for the synthesis of longer, higher quality DNA molecules than is possible with the first method. Also, the nucleic acid molecules synthesized according to the second method can be purified prior to the coupling step. Therefore, the quality of the nucleic acid molecule array can be expected to be much higher than the quality of the nucleic acid array of the first method.

5.1.3. Immobilization to a Solid Phase

Several methods have been proposed as suitable for immobilizing an oligonucleotide to a solid support. For example, Holmstrom, K. et al. (1993, Anal. Biochem. 209:278–283) exploit the affinity of biotin for avidin and streptavidin, and immobilize biotinylated nucleic acid molecules to avidin/streptavidin coated supports. Another method requires the pre-coating of the polystyrene or glass solid phases with poly-L-Lys or poly L-Ly,Phe, followed by the covalent attachment of either amino- or sulfhydryl-modified oligonucleotides using bi-functional crosslinking reagents. Both methods require the use of modified oligonucleotides as well as a pretreatment of the solid phase (see, e.g., Running, J. A. et al., 1990, BioTechniques 8:276–277; Newton, C. R. et al., 1993, Nucl. Acids Res. 21:1155–1162).

Kawai, S. et al. (1993, Anal. Biochem. 209:63–69) describes an alternative method in which short oligonucleotide probes were ligated together to form multimers, and these were ligated into a phagemid vector. The oligonucleotides were immobilized onto polystyrene plates and fixed by UV irradiation at 254 nm. A method for the direct covalent attachment of short, 5'-phosphorylated primers to chemically modified polystyrene plates ("Covalink" plates, Nunc) has also been proposed by Rasmussen, S. R. et al. (1991, Anal. Biochem. 198:138–142). The covalent bond between the modified oligonucleotide and the solid phase surface is created by a condensation reaction with a water-soluble carbodiimide. The Rasmussen method claims a predominantly 5'-attachment of the oligonucleotides via their 5'-phosphates; however, it requires the use of specially prepared, expensive plates.

Maskos, U. et al. (1992, Nucl. Acids Res. 20:1679–1684) describes a method to synthesize oligonucleotides directly onto a glass support. According to this method, a flexible linker with a primary hydroxyl group is bound to the solid support via a glycidoxypropyl silane, wherein the primary hydroxyl group serves as the starting point for the oligonucleotide synthesis. The disadvantages of this method are that the reaction is not reversible and the oligonucleotides leak from the solid surface during manipulation.

Covalent disulfide bonds have been previously used to immobilize both proteins and oligonucleotides. For example, Carlsson, J. et al. (1991, Biotech. Applied Biochem. 14:114–120) discloses a method for the reversible immobilization of thiolated proteins and peptides to an agarose bead by means of a disulfide bond. In that method, the disulfide bond is formed between a thiol containing protein and a thiol-derivatized agarose bead. The reference also discloses that the disulfide bond is reversible in the presence of an excess of dithiothreitol. Chu, B. C. F. et al. (1988, Nucl. Acids Res. 16:3671–3691) discloses a method for coupling oligonucleotides to nucleic acids or proteins via cleavable disulfide bonds. Prior to the coupling reaction, the oligonucleotides are modified by adding a cystamine group to the 5' phosphate by means of a phosphoramadite bond. Sliwkowski, M. X. et al. (1983, Biochem. J. 209:731–739) discloses a method of covalent chromatography wherein proteins are immobilized to cysteinylsuccinimidoproyl glass beads through reversible disulfide bond interaction.

Fahy, E. et al. (1993, Nucl. Acids Res. 21:1819–1826) describes the synthesis of 5'-bromacetyl and 5'-thiol oligonucleotide derivatives and the covalent immobilization of these oligonucleotide derivatives via thioester bonds to sulfhydryl- and bromacetyl-modified polyacrylamide supports. The disadvantage of this method is that the covalent bond is not reversible.

Anderson et al. (U.S. Ser. No. 08/812,010, filed on Mar. 5, 1997) describes a novel method for immobilizing nucleic acid molecules to a solid-phase by means of a reversible, covalent disulfied bond. In that method, a disulfide bond is formed between a thiol or disulfide containing nucleic acid molecule and a mercaptosilane coated solid surface. Shi et al. (U.S. Ser. No. 08/870,010) describes a novel method for immobilizing nucleic acid molecules to a solid phase by means of a covalent ether or thioether linkage. These simple, two-step methods have the specificity and efficiency needed to prepare DNA arrays.

All of the above described methods can be used in the present invention to immobilize the sequence reagent to the solid support, the preferred embodiments are those disclosed by Anderson et al. (supra), and by Shi et al. (supra). An additional preferred embodiment for immobilizing the sequencing reagent is to immobilize biotinylated nucleic acid molecules to avidin/streptavidin coated supports as disclosed by Holmstrom, K. et al. (1993, Anal. Biochem. 209:278–283).

Although any of a variety of glass or plastic solid supports can be used in accordance with the methods of the present invention, silicon glass is the preferred solid support. Preferably, the solid support is fashioned with array densities greater than 1000 elements/cm$^2$. The support can also be fashioned as a bead, dipstick, test tube, pin, membrane, channel, capillary tube, column, or as an array of pins or glass fibers. Preferably, the plastic support is a form of polystyrene plastic. Alternatively, the solid support can be glass, preferably in the form of a microscope slide, coverslip, a capillary tube, a glass bead, or a channel. The solid support can also be a glass plate, a quarts wafer, a nylon or nitrocellulose membrane, or a silicon wafer.

5.1.4. Array Formation

In the methods of the present invention, the sequence reagents are intended to be made into an array. As used herein, an array is an orderly, spatially dependent arrangement of sequence reagents, as in a matrix of rows and columns, or a spatially addressable or separable arrangement such as with coated beads. Preferably, the array is an array of permutations of the primer sequences, such as all possible 3mers, 4mers, 5mers, 6mers, 7mers, or combinations thereof.

With an automated delivery system, such as a Hamilton robot or ink-jet printing method, it is possible to form a very complex array of oligonucleotide primers on a solid support, in particular an epoxysilane, mercaptosilane, or disulfidesilane coated solid support. Such methods can deliver nano or pico-liter size droplets with sub-millimeter spacing. Because the aqueous beads are extremely well defined, it is possible to create an array with an extremely high density of oligonucleotide primers. Thus, it is possible to create arrays having greater than about 10,000 primer droplets/cm$^2$. Such arrays can be assembled through the use of a robotic liquid dispenser, such as an ink-jet printing device controlled by a piezoelectric droplet generator, such that each nucleic acid molecule occupies a spot of more than about 10 microns, preferably more than 25 microns in diameter, and such that each nucleic acid spot is spaced no closer, center to center, than the average spot diameter. Methods and apparatuses for dispensing small amounts of fluids using such ink-jet printing techniques and piezoelectric ink-jet depositions have been previously describe, e.g., by Wallace, D. B. et al. (U.S. Pat. No. 4,812,856) by Hayes, D. J. et al. (U.S. Pat. No. 5,053,100).

Under one embodiment, the array can be constructed using the method for Fodor, S. P. et al. (U.S. Pat. No. 5,445,934). Fodor et al. describes a method for constructing an array onto a solid surface wherein the surface is covered with a photoremovable group. Selected regions of the substrate surface are exposed to light so as to activate the selected regions. A monomer, which also contains a photoremovable group, is provided to the substrate surface to bind to the selected area. The process is repeated to create an array.

Under another preferred embodiment, the array can be created by means of a "gene pen". A gene pen, as used herein, refers to a mechanical apparatus comprising a reservoir for a reagent solution connected to a printing tip. The printing tip further comprises a means for mechanically controlling the solution flow. Under one embodiment, a multiplicity of gene pens or printing tips may be tightly clustered together into an array, with each tip connected to a separate reagent reservoir. Under another embodiment, discrete gene pens may be contained in an indexing turntable and printed individually. Typically, the solid surface is pretreated to enable covalent or non-covalent attachment of the reagents to the solid surface. Preferably, the printing tip is a porous pad.

Alternatively, the array can be created with a manual delivery system, such as a pipetman. Because these arrays are created with a manual delivery system, these arrays will not, in general, be as complex as those created with an automated delivery system. Arrays created with a manual delivery system will typically be spaced, center to center, $\geq 2$ mm apart. Depending on the delivery system employed, it is possible to create arrays spaced, center to center, with $\geq 2$ mm spacing, 0.5–2 mm spacing, 50–500 $\mu$m spacing, or $\leq 50$ $\mu$m spacing.

5.2. Polymerase Signaling Assay

The present invention provides methods for analyzing the sequence of a template nucleic acid molecule; i.e., for the detection and/or identification of particular nucleic acid sequences and/or subtypes thereof in a sample. Specifically, the invention provides methods for an assay, referred to herein as the polymerase signaling assay or PSA, for analyzing the sequence of a template nucleic acid molecule using the sequence arrays described in Section 5.2, above. The template nucleic acid molecule to be analyzed by the PSA methods of the invention may be from any source. For example, the template nucleic acid molecule may comprise a naturally occurring nucleic acid molecule such as a genomic or extragenomic DNA molecule isolated from an organism, or an mRNA molecule isolated from an organism. Alternatively, the template nucleic acid molecule may comprise a synthesized nucleic acid molecule, include a nucleic acid molecule synthesized enzymatically in vivo or in vitro. For example, the template nucleic acid molecule may comprise a cDNA molecule, or a nucleic acid molecule synthesized by PCR.

The template nucleic acid molecule may additionally be labeled with a detectable label, including the detectable labels described in Section 5.3.4, below. Preferably, the detectable label used to label the template nucleic acid molecule will be different from the label used to label the nucleotide or nucleotide analog for the primer extension reaction, so that the two moieties, i.e., the template molecule and the extended primer, can be readily distinguished from one another. Likewise, the detectable label used to label the template should preferably be different and distinct from any label used to label the primer sequence or the sequence reagent.

Preferably, the template nucleic acid molecule analyzed by the methods of this invention is a single stranded nucleic acid molecule, i.e., a single stranded template nucleic acid molecule or single stranded template. Accordingly, in embodiments wherein the initially provided is not single stranded, e.g., wherein a double stranded or triple stranded template nucleic acid molecule is initially provided, it is preferable to first treat the sample containing the template nucleic acid molecule so that a single stranded template nucleic acid molecule is thereby provided. However, the presence of an additional strand or strands does not necessarily have an adverse affect upon the methods of the invention. Accordingly, in other embodiments the template nucleic acid molecule may comprise nonsingle-stranded, e.g., double- or triple-stranded, nucleic acid molecules.

The template nucleic acid molecule additionally comprises a capture region, as described in Section 5.2, above, for the capture moiety. The capture region is capable of attaching itself to the capture moiety of the sequence reagents. The general steps of the polymerase signaling assay are illustrated in FIGS. 2A-C. The steps are described below, first briefly, and then in detail.

First, during template capture (FIG. 2A), the template nucleic acid molecule is contacted with the sequence reagents of the sequence array under conditions such that the capture region of the template molecule forms a stable complex with the capture moiety of a sequence reagent of the array. Second, in the template scanning (FIG. 2B) the template nucleic acid molecule and sequence reagent are incubated under conditions such that the primer region of the sequence reagent can identify complementary sequences, if any are present, in the template nucleic acid molecule. Finally, the primer is extended (FIG. 2C) by one or more additional nucleotides by a template dependent primer extension reaction mediated, e.g., by a DNA or RNA polymerase. The added nucleotides are detected to determine whether primer extension has occurred or not. The above methods are repeated for each sequence reagent of the sequence array, and the resultant pattern of primer extensions is then analyzed, e.g., by pattern comparison methods, to analyze the sequence of the template nucleic acid molecule.

It will be apparent to those of skill in the art, that in the most preferred embodiment the steps of the invention are repeated by contacting a sample comprising a plurality of the template nucleic acid molecule to be analyzed to the sequence array such that a template molecule is captured by each sequence reagent of the array, and polymerase extension is detected simultaneously for each sequence reagent. However, for simplicity the methods of the invention are described in terms of contacting a single template nucleic acid molecule to a single sequence reagent of an array. The steps of the PSA method of the invention a discussed individually, and in more detail below.

5.2.1. Generation of Single Stranded Templates

Preferably, the nucleic acid template molecules to be analyzed by the methods of the present invention will be provided as single stranded nucleic acid molecules. However, in certain embodiments template nucleic acid molecules may be provided that are not, initially, single stranded. For example, the template nucleic acid molecules to be analyzed by PSA may be double stranded, or triple stranded nucleic acid molecules. In such instances, the presence of an additional strand does not necessarily affect the polymerase signal assay of the invention. Thus, the methods of the present invention may be practiced on either double-stranded, or on single stranded DNA obtained, for example, by alkali treatment of native, double stranded DNA.

Where desired, however, any of a variety of methods can be used to eliminate one of the two natural strands of the target DNA molecule from the reaction. Single stranded DNA molecules may be produced using the single-stranded bacteriophage M13 (see, e.g., Messing, J. et al., 1983, *Meth. Enzymol.* 101:20; Samrook, J. et al., 1989, In: *Molecular Cloning: A Laboratory Manual*, Cold Spring Harbor Laboratory Press, Cold Spring Harbor, N.Y.).

Several alternative methods can be used to generate single-stranded DNA molecules. Gyllensten, U. et al. (1988, *Proc. Natl. Acad. Sci.* U.S.A. 85:7652–7656) and Mihovilovic M. et al. (1989, *Biotechniques* 7:14) describe a method, termed "asymmetric PCR", in which the standard PCR method is conducted using primers that are present in different molecular concentrations. Higuchi, R. G. et al. (1985, *Nucl. Acids Res.* 17:5865) exemplifies an additional method for generating single-stranded amplification products. The method entails phosphorylating the 5'-terminus of one strand of a double-stranded amplification product, and then permitting a 5'→3' exonuclease to preferentially degrade the phosphorylated strand.

Other methods have also exploited the nuclease resistant properties of phosphorothioate derivatives in order to generate single-stranded DNA molecules (see, e.g., Benkovic et al., U.S. Pat. No. 4,521,509; Sayers, J. R. et al., 1988, *Nucl. Acids Res.* 16:791–802; Eckstein, F. et al., 1976, *Biochemistry* 15:1685–1691; and Ott, J. et al., 1987, *Biochemistry* 26:8237–8241).

Most preferably, such single-stranded molecules will be produced using the methods described by Nikiforov, T. (U.S. Pat. No. 5,518,900). In brief, these methods employ nuclease resistant nucleotide derivatives, and incorporate such derivatives, by chemical synthesis or enzymatic means, into primer molecules, or their extension products, in place of naturally occurring nucleotides.

Suitable nucleotide derivatives include derivatives in which one or two of the non-bridging oxygen molecules of the phosphate moiety of a nucleotide has been replaced, e.g., with a sulfur-containing group such as a phosphorothioate, an alkyl group such as a methyl or ethyl alkyl group, a nitrogen-containing group such as an amine, and/or a selenium-containing group. Phosphorothioate deoxyribonucleotide or ribo-nucleotide derivatives are the most preferred nucleotide derivatives. Methods of producing and using such phosphorothioate derivatives are disclosed by Nikiforov, T. (U.S. Pat. No. 5,518,900).

5.2.2. Template Capture

Once a template nucleic acid molecule and sequence array have been provided, the first step of the PSA methods of the present invention is to contact the sample containing the template molecule with the sequence array under conditions such that the capture region of the template nucleic acid molecule forms a stable complex with the capture moiety of a sequence reagent. In particular, the capture region of the template molecule must form a stable complex with the capture moiety of the sequence reagent so that the template molecule is immobilized to the sequence reagent of the solid-phase sequence array.

The exact conditions necessary will be apparent to one of skill in the art for particular embodiments of the capture moiety and capture region. For example, in a particularly preferred embodiment, the capture moiety is a sequence of 8 to 24 cytosine bases which hybridizes to a capture region of 8 to 24 guanine bases incorporated in the template nucleic acid molecule. In another preferred embodiment, the capture moiety can be a specific sequence complementary to a PCR primer, or portion thereof, used to amplify a region of the template strand. Thus, in such embodiments appropriate hybridization conditions would be conditions of high stringency, e.g., incubation at a final template concentration of 100 nM in 1.5 M NaCl at room temperature for 1 hour, followed by multiple washings in 1×TNTw (Tris pH 8, Tween 0.5%, 150 mM NaCl).

In general, the efficiency of hybridization and the thermal stability of hybrids formed between such embodiments, wherein the capture region and capture moiety comprise a target nucleic acid sequence and a short oligonucleotide primer, respectively, depends strongly on the nucleotide sequence of the primer, and on the stringency of the reaction conditions as discussed, e.g., in Conner, B. J. et al., supra. Appropriate hybridization conditions for specific embodiments will therefore be apparent to those skilled in the art in view of the above and other references well known in the art.

5.2.3. Template Scanning

After the template nucleic acid molecule has been immobilized to the sequence reagent as described above, the template-reagent complex is incubated under conditions which allow duplex formation between the primer sequence of the sequence reagent and sequences of the template nucleic acid molecule that are complementary to the primer sequence. Such conditions generally comprise conditions of stringent hybridization, such as the conditions described above for hybridization of a target nucleic acid sequence and a short oligonucleotide primer or probe.

Primer sequences as short as 3–7 bases cannot hybridize to a template molecule to form stable duplexes. However, such primers will form transient duplexes in the presence of a polymerase with complementary regions of a template so that template dependent extension of the primer occurs. Such duplexes will only form between the template nucleic acid molecule and those sequence specific hybridization regions for which the complementary sequence is present, in one or more copies, in the template nucleic acid molecule.

5.2.4. Primer Extension

Preferably, before the primer extension reaction is performed, the template is capped by the addition of a terminator to the 3'-end of the template. The terminator is one which is capable of terminating a template-dependent, primer extension reaction. The template is thus capped so that no additional nucleotides or nucleotide analogs will attach to the 3'-end of the template. The 3'-end of the template may be capped, e.g., by a dideoxynucleotide, or by other chain terminating nucleotides, such as those described below, in Section 5.3.4.

The conditions for the template-dependent primer extension reaction require the presence of a suitable template dependent enzyme, such as a DNA or RNA polymerase. However, the polymerase must be both primer and template dependent. Preferably, the polymerase is also a thermostable and/or exonuclease free polymerase. Exemplary DNA polymerases which may be used in the methods of the invention include, for example, E. coli DNA pol I or the "Klenow fragment" thereof, T4 DNA polymerase, T7 DNA polymerase (i.e., "Sequenase"), T. aquaticus DNA polymerase, or a retroviral reverse transcriptase. RNA polymerases, such as T3 or T7 RNA polymerase, can also be used in certain embodiments.

The conditions for the template-dependent primer extension reaction further require the presence of any one or more "nucleotide moieties", i.e., one or more of the naturally occurring nucleotides or analogs thereto. Preferably, the duplexes are incubated in the presence of all four of the natural deoxynucleoside triphosphates (dNTP's), dATP, dCTP, dGTP, and dTTP, or in the presence of analogues to all four of the above dNTP's. Alternatively, one or more of the nucleotide moieties may comprise a ribonucleotide triphosphate (rNTP) In one embodiment, the template-primer duplex is incubated in the presence of non-extendible or chain terminating nucleotides. Exemplary chain terminating nucleotides include 2',3'-dideoxynucleotide triphosphate derivatives of adenine, thymine cytosine, and guanine.

In addition to dideoxynucleotides, 3'phosphate modified oligonucleotides which are complementary to a template nucleic acid molecule and effectively block DNA polymerization, can be used in the present invention (see, e.g., Kornberg et al., 1992, In: *DNA Replication*, 2nd Edition, Kornberg et al., eds., W. H. Freeman & Co., San Francisco, pp. 408, 446–449). Alternatively, a nucleotide analog, such as a fructose based nucleotide analog or a chemically modified purine or pyrimidine that retains the ability to specifically base pair with naturally occurring nucleotides may be used to block DNA polymerization. A variety of 3'-substituted nucleotides (see, e.g., Antrazhev, 1987, *Bioorg. Khim* 13:1045–52; Chidgeavadze, Z. G. et al., 1986, *Biochemi. Biophys.* Acta 868:145–152; Chidzhacadze et. al., 1989, *Mol. Biol.* (*Mosk.*) 23:1732–1742) such as azido-(Mitsuya et al., 1986, *Proc. Natl. Acad. Sci. U.S.A.* 83:1191), mercapto- (Yuzhakov et al., 1992, *FEBS Letters* 306:185–188), amino- (Herrein et al., 1994, *Helvetica Chimica Acta* 77:586–596), and fluoro- (Chidgeavadze, Z. G. et al., 1985, *FEBS Letters* 183:275–278) substituted nucleotides, which have been reported to terminate DNA synthesis, can be used in the present invention.

The nucleotide or nucleotide analog can be detectably labeled, preferably with a fluorescent molecule or haptenated deoxy- or dideoxynucleotide. Alternatively, the nucleotide can be detected, e.g., using delayed extraction MALDI-TOF mass spectrometer (see, e.g., Haff, L. A. et al., 1997, *Genome Methods* 7:378–388). MALDI-TOF mass spectrometry is capable of determining the identity of the incorporated non-extendible nucleotide by the change in mass of the extended primer.

The use of fluorescently labeled nucleotides and nucleotide analogues in more preferable. Other labels suitable for use in the present invention include, but are not limited to, biotin, iminobiotin, antigens, cofactors, dinitrophenol, lipoic acid, olefinic compounds, detectable polypeptides, electron rich molecules, enzymes capable of generating a detectable signal, and radioactive isotopes. The preferred radioactive isotopes include $^{32}P$, $^{35}S$, $^{14}C$, and $^{25}I$. Fluorescent molecules suitable for the present invention include, but are not limited to, fluorescein, rhodamine, texas red, FAM, JOE, TAMRA, ROX, HEX, TET, Cy3, Cy3.5, Cy5, Cy5.5, IRD40, IRD41, and BODIPY. As used herein, "FAM" refers to 5'carboxy-fluorescein, "JOE" refers to 2',7'-dimethoxy-4',5'-dichloro-6-carboxy-fluorescein, "TAMRA" refers to N,N,N',N'-tetramethyl-6-carboxy-rhodamine, "ROX" refers to 6-carboxy-X-rhdoamine. Electron rich indicator molecules suitable for the present invention include, but are not limited to, ferritin, hemocyanin, and colloidal gold. Alternatively, the polypeptide may be indirectly detected by specifically complexing a first group to the polypeptide. A second group, covalently linked to an indicator molecule, which has affinity for the first group could be used to detect the polypeptide. In such an embodiment, compounds suitable for use as a first group include, but are not limited to, avidin and strepavidin. Compounds suitable for use as a second group include, but are not limited to, biotin and iminobiotin.

The exact conditions necessary for the template-dependent primer extension reaction will be determined by the specific polymerase used for the reaction, as well as by the choice of nucleotide or nucleotide analogues. These conditions for specific embodiments of the primer extension reaction will be apparent to those of skill in the art.

In one preferred embodiment, the template nucleic acid molecule is separated from the sequence reagent after the extension reaction. This embodiment thus allows the template to be recovered, e.g., for further analysis. The template molecule is separated from the sequence reagent by means of appropriate denaturing conditions that are well known to those of skill in the art; e.g., incubating the template-reagent complex with heat, alkali, formamide, urea, glyoxal, enzymes, and combinations thereof.

5.2.5. Detection and Analysis

Once polymerase extension products have been permitted to form, the extension product is detected for each sequence reagent. For embodiments wherein labeled nucleotides or nucleotide analogues are used in the primer extension reaction, signal detection consists of simply detecting the labeled nucleotide.

For example, in embodiments wherein fluorescently labeled nucleotides or nucleotide analogues are used, signal detection is accomplished simply by detecting a fluorescent signal at the wavelength emitted by the fluorophore. In other embodiments, wherein the nucleotide or nucleotide analogues are labeled by means of radioactive isotopes, e.g., $^{32}P$ or $^{35}S$ labeled dNTP's or ddNTP's, extension products may be detected by using autoradiography to detect the radioactive base. In yet other embodiments which use chemical labels such as biotin, the labeled nucleotide or nucleotide analog may be detected, e.g., by means of a fluorescent probe or dye such as RPE Protein Dye (Molecular Probe).

The results of signal detection for an array of sequence reagents, each of which comprises a unique primer sequence, can be represented as a digital matrix or pattern of binary "on/off" values for each sequence reagent of the sequence array wherein either an extension product is detect ("on"-value) or no extension product is detected ("off"-value). Each binary signal of the resulting matrix thus indicates that are particular primer sequence is ("on") or is not ("off") present in the template nucleic acid molecule. The nucleotide sequence of the template molecule is thereby represented as a unique digital pattern.

Such digital data can readily be stored as binary patterns in a computer readable format and loaded into computer memory for further manipulation or analysis. The binary patterns can be readily analyzed by simply comparing them, e.g., to the known binary patterns of other wild type of mutation nucleotide sequences. Such comparisons can be made simply by the manual inspection of such patterns by a user, or by means of a computer algorithm using the binary pattern read into computer memory.

Known binary patterns can be readily obtained, e.g., by applying the above methods of PSA to a template nucleic acid molecule consisting of a known wild type or mutation sequence. Alternatively, the binary pattern of a known wild type or mutation sequence can be predicted from its nucleic acid sequence.

Sequences of approximately 300–500 bases can be analyzed by the above methods using arrays of 1024 unique sequence reagent comprising primer sequences of 5 bases with a high probability of detecting and characterizing all possible mutations within the sequence. Nucleotide sequences of about 100 bases can be analyzed using 256 element arrays having primer sequences four bases in length. Arrays of comprising primer sequences six bases in length are appropriate for characterizing template nucleic acid molecules of about 500–1,500 bases.

6. EXAMPLES

The examples presented here illustrate the concept and practice of the polymerase signaling assay methods of the invention. Specifically, the examples first demonstrate the application of the methods of the invention to comparatively analyzing the sequences of a "wild type" and "mutant" DNA oligonucleotide sequence. The examples demonstrate, second, the use of the polymerase signaling assay methods of the invention to analyze template nucleic acid molecules corresponding to an exon of the p53 gene, including template nucleic acid molecules corresponding to mutant and polymorphic sequences of that gene.

The examples are presented by way of illustration of the previously described invention, and are not limiting of that description in any way.

6.1. Example 1

Use of PSA to Identify Single Base Substitutions in a Synthetic Template

This example analyzes two synthetic DNA templates that vary by a single base using the Polymerase Signaling Assay (PSA) method of the present invention on a solid-phase sequence array. The results of this example demonstrate that the PSA methods of the present invention produce different patterns of signals for the two different template sequences as predicted.

6.1.1. Materials and Methods

Template Synthesis:

DNA oligonucleotide sequences which are complementary to the "wild type" and "mutant" sequences listed in Table I were synthesized using standard techniques of phosphoramidite chemistry (see, e.g., Matteucci, M. D. et al., supra) as templates for PSA analysis. The oligonucleotides were synthesized to further contain a 5'-(C)$_{18}$ (SEQ ID NO.4) tail to provide a capture region for attachment of the template to the sequence reagents.

Primer Synthesis:

The 21 primer sequences shown in Table II were synthesized using the same phosphoramidite chemistry techniques as were used for template synthesis, describe above. The primers were synthesized to additionally contain a 5'-(G)$_{18}$-(N)$_7$ (SEQ ID NO.3) tail of 2'-O-Me RNA nucleotides which functioned as a capture, and spacer region for the sequence reagent. A thiol group was incorporated at the 5'-terminus of the sequence reagent to function as an attachment moiety to secure the reagent to the glass surface of the sequence array.

Array Formation:

The 21 sequence reagents were printed in a five by five array on glass slides, according to the methods described in Section 5.2.3 and 5.2.4, above.

Polymerase Signal Assay:

Each template was attached to the sequence array by incubation at a final concentration of 100 nM in a 1.5 M NaCl solution at room temperature for 1 hour. Slides were washed three times in 1×TNTw (Tris pH 8, Tween 0.5%, NaCl 150 mM) followed by incubation with an extension mix (described in Head, S. et al., 1997, supra) in which all four ddNTP's were labeled with Biotin. After 30 minutes at room temperature, the extension reaction was terminated by washing the slides three times in 1×TNTw. 300 μg of RPE Protein Dye (Molecular Probes) was incubated on each array for 30 minutes, the arrays were washed and scanned on a Hitachi FMBIO.

6.1.2. Results

The purpose of this experiment was to analyze two template DNA molecules that vary by a single nucleotide base using the PSA methods of the present invention. To this end, two template deoxyribo-oligonucleotide sequences were synthesized having the nucleotide sequences listed in Table I. For convenience, the two sequences are referred to herein as the "wild type" and "mutant" sequences, respectively. The two sequences differed by only one nucleotide base; specifically by the substitution of a guanine for cytosine at position 8 of the wild type sequence shown in Table I. This single nucleotide polymorphisms is indicated in Table I by the underlined base in each of the two sequences. The two template sequence also had 5'-(C)$_{18}$ (SEQ ID NO.4) tails to function as the capture region for attachment to the capture moiety of the sequence reagent.

TABLE I

| | |
|---|---|
| wild type sequence (SEQ. ID NO. 1) | 5'-GTCTCTC<u>C</u>CAGGACAGGCACA-3' |
| mutant sequence (SEQ. ID NO. 2) | 5'-GTCTCTC<u>G</u>CAGGACAGGCACA-3' |

A sequence array was constructed for sequence analysis of each of the two templates according to the methods described in Section 5.2, above. The sequence reagents used in the array had the schematic structure.

S·S–(G)$_{18}$–(N) (SEQ ID NO.3)–NXXXXX wherein a disulfide bond (S·S) functioned as the attachment moiety, a (G)$_{18}$ base sequence functioned as the capture moiety, and a string of seven mixed bases ((N)$_7$) functioned as the spacer region. 2'-O-Me RNA bases were used for the nucleotides of both the capture moiety and the spacer region. The primer sequence of each sequence reagent comprised a specific base sequence of four nucleotides which functioned as primers to the templates during the assay. The sequence reagents were printed in a five by five array on glass slides, according to the methods described in Section 5.2, above.

Twenty-one primer sequences were used in the assay which had signal sequences found in both the wild type and mutant templates. Their sequences are listed in Table II, below, along with the coordinates of their location in the sequence array. Table II further indicates whether primer extension is predicted for each of the 21 primer sequences, i.e., whether the five base primer sequence is present in either the wild type or mutant template sequence.

TABLE II

| Primer Location | Signal Sequence | Expect Signal from Wild Type | Expect Signal from Mutant |
|---|---|---|---|
| A2 | CCTGC SEQ. ID NO. 5 | NO | YES |
| A3 | TGTCG SEQ. ID NO. 6 | YES | YES |
| A4 | GTGCC SEQ. ID NO. 7 | YES | YES |
| B1 | TGCCT SEQ. ID NO. 8 | YES | YES |
| B2 | GCCTG SEQ. ID NO. 9 | YES | YES |
| B3 | CCTGT SEQ. ID NO. 10 | YES | YES |
| B4 | CTGCG SEQ. ID NO. 11 | NO | YES |
| B5 | CTGTC SEQ. ID NO. 12 | YES | YES |
| C1 | TGTCC SEQ. ID NO. 13 | NO | YES |
| C2 | CGAGA SEQ. ID NO. 14 | YES | YES |
| C3 | GTCCT SEQ. ID NO. 15 | YES | YES |
| C4 | TCCTG SEQ. ID NO. 16 | YES | YES |
| C5 | CCTGG SEQ. ID NO. 17 | YES | NO |
| D1 | CTGGG SEQ. ID NO. 18 | YES | NO |
| D2 | TGGGA SEQ. ID NO. 19 | YES | YES |
| D3 | TGCGA SEQ. ID NO. 20 | NO | YES |
| D4 | GGGAG SEQ. ID NO. 21 | YES | NO |
| D5 | GGAGA SEQ. ID NO. 22 | YES | NO |
| E2 | GAGAG SEQ. ID NO. 23 | YES | YES |
| E3 | AGAGA SEQ. ID NO. 24 | YES | YES |
| E4 | GCGAG SEQ. ID NO. 25 | NO | YES |

The expected data signals for the assay are illustrated graphically in FIG. 3A for the wild type template molecule, and in FIG. 3C for the mutant template molecule.

The resultant experimental data patterns from PSA analysis of the template molecules are shown in FIGS. 3B and 3D. FIG. 3B shows the resultant digital matrix from PSA analysis of the wild type sequence, while FIG. 3D shows the digital matrix obtained from PSA analysis of the mutant sequence. The two arrays show distinct signal patterns reflective of the sequence of the two different templates.

6.2. Example 2

Use of PSA to Identify Mutations and Polymorphisms in a P53 Gene

This example analyzes the 103 base pair sequence of p53 exon 8 using the PSA methods of the present invention on a solid-phase sequence array. The results of this example demonstrate that the PSA methods of the invention can identify several varieties of genetic mutations and/or polymorphisms of an actual gene, including single nucleotide polymorphisms, base deletions, base insertions, and heterozygote polymorphisms.

The purpose of this experiment was to determine the potential applicability of the PSA methods of the invention for analyzing template nucleic acid molecules corresponding to actual genetic sequences. To this end, the PSA methods were used to analyze wild type and mutant sequences of the 106 base exon 8 of the p53 gene (SEQ ID NO.1 & SEQ ID NO.2).

Accordingly, using a computer model, expected binary data was generated for PSA analysis of every possible point mutation of the p53 exon 8 nucleic acid sequences, thereby generating data for 3×106=318 different nucleic acid sequences. The predicted digital matrices are illustrated in FIGS. 4A–6C for certain, specific sequences.

The results show that about 97% of the mutations could be characterized for the p53 exon 8 sequence of approximately 100 bases using a 256 primer array of 4 base primers. The expected digital array generated by the wild type sequence of p53 exon 8 is illustrated schematically in FIG. 4A, while FIG. 4B illustrates the expected digital array generated by a mutant sequence wherein the nucleotide 38C has been converted to a T. The difference between the two digital matrices is show in FIG. 4C, demonstrating that this single nucleotide polymorphisms generates a unique digital pattern which enables it to be distinguished from the wild type sequence by the PSA methods of the invention. FIGS. 5A–C show similar results for the single nucleotide polymorphism wherein the nucleotide 38C is transverted to an A, demonstrating that this sequence also generates an unique digital pattern enabling it to be characterized by the PSA methods of the invention.

FIGS. 6A–C illustrate the results of the experiment for a p53 exon 8 template sequence having a heterozygous polymorphism. The heterozygous template contains two alleles of the p53 exon 8 nucleotide sequence. The first allele comprises the wild type p53 exon 8 sequence, while the second allele comprises the SNP described for FIG. 4B, above; i.e., the SNP wherein the base 38C is converted to a T. This heterozygous template produces a unique digital matrix which can be readily distinguished from the digital signal produced by PSA analysis of the wild type sequence, as illustrated in FIG. 6C which shows the difference between the two signals. Further, as evidenced by a visual inspection of the two figures, the signal generated by the heterozygous SNP and illustrated in FIG. 6B is also unique from the homozygous SNP's PSA signal pattern illustrated in FIG. 4B.

Expected binary data was also generated for PSA analysis of p53 exon 8 sequences having base deletions, insertions, or heterozygous mutations. These results are illustrated in FIGS. 7A–8C. Specifically, FIG. 7B illustrates the binary signal pattern predicted for PSA analysis of a p53 exon 8 template nucleic acid molecule having a five base deletion. The predicted signal for the wild type p53 exon 8 sequence is illustrated in FIG. 7A, and their difference is shown in FIG. 7C. Likewise, FIG. 8B illustrates the binary signal pattern predicted for PSA analysis of a p53 exon 8 template containing a five base insertion, and FIG. 5C compares this signal with that of the wild type p53 exon 8 sequence, illustrated in FIG. 8A. The results show that these mutations generate signal which enable them to also be uniquely characterized by the PSA methods of the present invention.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for analyzing the sequence of a template comprising:
   a) capturing the template with a sequencing reagent to form a captured template, said sequencing reagent being immobilized to a solid surface and comprising:
      (i) a capture moiety capable of forming a stable duplex with a region of the template nucleic acid molecule;
      (ii) a primer region comprising from 3 to 7 bases; and between said capture moiety and said primer region
      (iii) a spacer region that minimizes template independent noise; and
   b) scanning the captured template using a primer-polymerase complex for regions of complementarity to the primer region and forming a duplex;
   c) extending the primer region by at least one nucleotide moiety by means of a template-homology dependent extension reaction to form an extended primer; and
   d) detecting the extended primer, wherein said detecting of the extended primer indicates the presence of one or more regions of complementarity to the primer region in the captured template;
   wherein the steps of the method are repeated for sequencing reagents that are bound in an array pattern onto to said solid surface so that a pattern of signals is generated for the template.

2. The method of claim 1, wherein the solid surface is glass or plastic.

3. The method of claim 1, wherein the solid surface is a glass plate, a quartz wafer, a nylon membrane, a nitrocellulose membrane, or a silicon wafer.

4. The method of claim 1, wherein the solid surface is silicon glass.

5. The method of claim 1, wherein the solid surface is polystyrene plastic.

6. The method of claim 1, wherein the sequencing reagent further comprises an attachment moiety.

7. The method of claim 6, wherein the sequence reagent has a 5'-terminus and the attachment moiety is located at or near said 5'-terminus.

8. The method of claim 6, wherein the attachment moiety is an amino group, a thiol group, a disulfide group, or a biotin group.

9. The method of claim 1, wherein the capture moiety comprises a sequence of 8–24 cytosine bases.

10. The method of claim 1, wherein the capture moiety comprises a specific sequence complementary to a PCR primer or a portion thereof.

11. The method of claim 1, wherein the spacer region is at least 10 nm in length.

12. The method of claim 1, wherein the spacer region comprises a random, pseudo-random, or non-random sequence of nucleotide bases or analogs thereof.

13. The method of claim 1, wherein the at least one nucleotide moiety is a non-chain terminating nucleotide or an analogue of a non-chain terminating nucleotide.

14. The method of claim 13, wherein the at least one nucleotide moiety is a deoxynucleoside triphosphate base or ribonucleoside triphosphate base.

15. The method of claim 13, wherein the at least one nucleotide moiety is a chain terminating nucleotide analogue.

16. The method of claim 15, wherein the chain terminating nucleotide analogue is a dideoxynucleotide.

17. The method of claim 1, wherein the at least one nucleotide moiety has a detectable labeled.

18. The method of claim 17, wherein the detectable label is a fluorescent label.

19. The method of claim 17, wherein the detectable label is a radioactive isotope.

20. The method of claim 17, wherein the detectable label is an electron rich molecule.

21. The method of claim 1, wherein the extended primer is detected by change in mass.

22. The method of claim 1, wherein the density of sequence reagents in the array is at least 1000 elements/cm$^2$.

23. The method of claim 21, wherein said change in mass is detected through mass spectrometry.

24. The method of claim 1, wherein said primer region consists of from 4 to 6 bases.

25. The method of claim 1, wherein the spacer is comprised of one or more of PNA sequences, glycol groups or 5'-nitroindole groups.

* * * * *

SEQUENCE LISTING

```
<160> NUMBER OF SEQ ID NOS: 25

<210> SEQ ID NO 1
<211> LENGTH: 21
<212> TYPE: DNA
<213> ORGANISM: Artificial Sequence
<220> FEATURE:
<223> OTHER INFORMATION: Synthetic Template

<400> SEQUENCE: 1
gtctctccca ggacaggcac a                                             21

<210> SEQ ID NO 2
<211> LENGTH: 21
<212> TYPE: DNA
<213> ORGANISM: Artificial Sequence
```

```
<220> FEATURE:
<223> OTHER INFORMATION: Synthetic Template

<400> SEQUENCE: 2
gtctctcgca ggacaggcac a                                              21

<210> SEQ ID NO 3
<211> LENGTH: 25
<212> TYPE: DNA
<213> ORGANISM: Artificial Sequence
<220> FEATURE:
<223> OTHER INFORMATION: Synthetic Reagent Capture and Spacer Regions
<221> NAME/KEY: misc_feature
<222> LOCATION: (19)..(25)
<223> OTHER INFORMATION: n is atc or g

<400> SEQUENCE: 3
gggggggggg ggggggggnn nnnnn                                          25

<210> SEQ ID NO 4
<211> LENGTH: 18
<212> TYPE: DNA
<213> ORGANISM: Artificial Sequence
<220> FEATURE:
<223> OTHER INFORMATION: Synthetic Capture Region

<400> SEQUENCE: 4
cccccccccc cccccccc                                                  18

<210> SEQ ID NO 5
<211> LENGTH: 5
<212> TYPE: DNA
<213> ORGANISM: Artificial Sequence
<220> FEATURE:
<223> OTHER INFORMATION: Synthetic Primer

<400> SEQUENCE: 5 cctgc                                                                 5

<210> SEQ ID NO 6
<211> LENGTH: 5
<212> TYPE: DNA
<213> ORGANISM: Artificial Sequence
<220> FEATURE:
<223> OTHER INFORMATION: Synthetic Primer

<400> SEQUENCE: 6 tgtgc                                                                 5

<210> SEQ ID NO 7
<211> LENGTH: 5
<212> TYPE: DNA
<213> ORGANISM: Artificial Sequence
<220> FEATURE:
<223> OTHER INFORMATION: Synthetic Primer

<400> SEQUENCE: 7 gtgcc                                                                 5

<210> SEQ ID NO 8
<211> LENGTH: 5
<212> TYPE: DNA
<213> ORGANISM: Artificial Sequence
<220> FEATURE:
<223> OTHER INFORMATION: Synthetic Primer

<400> SEQUENCE: 8
```

| | |
|---|---|
| tgcct | 5 |

<210> SEQ ID NO 9
<211> LENGTH: 5
<212> TYPE: DNA
<213> ORGANISM: Artificial Sequence
<220> FEATURE:
<223> OTHER INFORMATION: Synthetic Primer

<400> SEQUENCE: 9

| | |
|---|---|
| gcctg | 5 |

<210> SEQ ID NO 10
<211> LENGTH: 5
<212> TYPE: DNA
<213> ORGANISM: Artificial Sequence
<220> FEATURE:
<223> OTHER INFORMATION: Synthetic Primer

<400> SEQUENCE: 10

| | |
|---|---|
| cctgt | 5 |

<210> SEQ ID NO 11
<211> LENGTH: 5
<212> TYPE: DNA
<213> ORGANISM: Artificial Sequence
<220> FEATURE:
<223> OTHER INFORMATION: Synthetic Primer

<400> SEQUENCE: 11

| | |
|---|---|
| ctgcg | 5 |

<210> SEQ ID NO 12
<211> LENGTH: 5
<212> TYPE: DNA
<213> ORGANISM: Artificial Sequence
<220> FEATURE:
<223> OTHER INFORMATION: Synthetic Primer

<400> SEQUENCE: 12

| | |
|---|---|
| ctgtc | 5 |

<210> SEQ ID NO 13
<211> LENGTH: 5
<212> TYPE: DNA
<213> ORGANISM: Artificial Sequence
<220> FEATURE:
<223> OTHER INFORMATION: Synthetic Primer

<400> SEQUENCE: 13

| | |
|---|---|
| tgtcc | 5 |

<210> SEQ ID NO 14
<211> LENGTH: 5
<212> TYPE: DNA
<213> ORGANISM: Artificial Sequence
<220> FEATURE:
<223> OTHER INFORMATION: Synthetic Primer

<400> SEQUENCE: 14

| | |
|---|---|
| cgaga | 5 |

<210> SEQ ID NO 15
<211> LENGTH: 5
<212> TYPE: DNA

```
<213> ORGANISM: Artificial Sequence
<220> FEATURE:
<223> OTHER INFORMATION: Synthetic Primer

<400> SEQUENCE: 15 gtcct                                                                     5

<210> SEQ ID NO 16
<211> LENGTH: 5
<212> TYPE: DNA
<213> ORGANISM: Artificial Sequence
<220> FEATURE:
<223> OTHER INFORMATION: Synthetic Primer

<400> SEQUENCE: 16 tcctg                                                                     5

<210> SEQ ID NO 17
<211> LENGTH: 5
<212> TYPE: DNA
<213> ORGANISM: Artificial Sequence
<220> FEATURE:
<223> OTHER INFORMATION: Synthetic Primer

<400> SEQUENCE: 17 cctgg                                                                     5

<210> SEQ ID NO 18
<211> LENGTH: 5
<212> TYPE: DNA
<213> ORGANISM: Artificial Sequence
<220> FEATURE:
<223> OTHER INFORMATION: Synthetic Primer

<400> SEQUENCE: 18 ctggg                                                                     5

<210> SEQ ID NO 19
<211> LENGTH: 4
<212> TYPE: DNA
<213> ORGANISM: Artificial Sequence
<220> FEATURE:
<223> OTHER INFORMATION: Synthetic Primer

<400> SEQUENCE: 19 tgga                                                                      4

<210> SEQ ID NO 20
<211> LENGTH: 5
<212> TYPE: DNA
<213> ORGANISM: Artificial Sequence
<220> FEATURE:
<223> OTHER INFORMATION: Synthetic Primer

<400> SEQUENCE: 20 tgcga                                                                     5

<210> SEQ ID NO 21
<211> LENGTH: 5
<212> TYPE: DNA
<213> ORGANISM: Artificial Sequence
<220> FEATURE:
<223> OTHER INFORMATION: Synthetic Primer

<400> SEQUENCE: 21 gggag                                                                     5
```

```
<210> SEQ ID NO 22
<211> LENGTH: 5
<212> TYPE: DNA
<213> ORGANISM: Artificial Sequence
<220> FEATURE:
<223> OTHER INFORMATION: Synthetic Primer

<400> SEQUENCE: 22 ggaga                                                              5

<210> SEQ ID NO 23
<211> LENGTH: 5
<212> TYPE: DNA
<213> ORGANISM: Artificial Sequence
<220> FEATURE:
<223> OTHER INFORMATION: Synthetic Primer

<400> SEQUENCE: 23 gagag                                                              5

<210> SEQ ID NO 24
<211> LENGTH: 5
<212> TYPE: DNA
<213> ORGANISM: Artificial Sequence
<220> FEATURE:
<223> OTHER INFORMATION: Synthetic Primer

<400> SEQUENCE: 24 agaga                                                              5

<210> SEQ ID NO 25
<211> LENGTH: 5
<212> TYPE: DNA
<213> ORGANISM: Artificial Sequence
<220> FEATURE:
<223> OTHER INFORMATION: Synthetic Primer

<400> SEQUENCE: 25 gcgag                                                              5
```